US007553387B2

(12) United States Patent
Leeflang et al.

(10) Patent No.: US 7,553,387 B2
(45) Date of Patent: Jun. 30, 2009

(54) CATHETERS WITH LUBRICIOUS LININGS AND METHODS FOR MAKING AND USING THEM

(75) Inventors: Stephen A. Leeflang, Sunnyvale, CA (US); Christian S. Eversull, Palo Alto, CA (US); Nicholas J. Mourlas, Mountain View, CA (US); Christine P. Ventura, San Jose, CA (US)

(73) Assignee: ILH, LLC, Palo Alto, CA (US)

( * ) Notice: Subject to any disclaimer, the term of this patent is extended or adjusted under 35 U.S.C. 154(b) by 339 days.

(21) Appl. No.: 11/340,904

(22) Filed: Jan. 26, 2006

(65) Prior Publication Data

US 2007/0074805 A1 Apr. 5, 2007

Related U.S. Application Data

(60) Provisional application No. 60/723,300, filed on Oct. 4, 2005.

(51) Int. Cl.
*B32B 37/00* (2006.01)
(52) U.S. Cl. .................. 156/217; 156/203; 156/84; 156/86; 156/244; 156/18; 156/85; 156/218; 156/216; 156/184; 156/278; 156/251; 604/19; 604/523; 604/265; 428/36; 427/2.1
(58) Field of Classification Search ................ 156/203, 156/84, 86, 244.18, 85, 218, 217, 216, 184, 156/278, 251; 604/19, 523, 265; 428/36; 427/2.1
See application file for complete search history.

(56) References Cited

U.S. PATENT DOCUMENTS 3,879,516 A 4/1975 Wolvek (Continued)

FOREIGN PATENT DOCUMENTS

WO 9113648 9/1991

(Continued)

OTHER PUBLICATIONS

PCT International Search Report for PCT/US2006/039074, Applicant: ILH, LLC, Forms PCT/ISA/210 and PCT/ISA/220, dated May 23, 2007, 10 pages.

(Continued)

*Primary Examiner*—Jeff Aftergut
*Assistant Examiner*—Jaeyun Lee
(74) *Attorney, Agent, or Firm*—William A. English; Vista IP Law Group LLP

(57) ABSTRACT

A method for making a tubular device includes coating a first surface of a thin sheet, rolling the sheet such that side edges of the sheet are disposed adjacent one another with the coating disposed inwardly, creating a longitudinal seam along the side edges to create a sleeve, and attaching a tubular structure around the sleeve. In another embodiment, the method includes coating a first surface of a thin sheet, wrapping the sheet partially around a mandrel with the coating disposed inwardly, positioning a slotted tube around the sheet and mandrel, attaching the tube to the thin, and trimming any excess material of the sheet. In another embodiment, the method includes coating an outer surface of a thin sleeve, inverting the sleeve, and attaching a tubular structure around the inverted sleeve, thereby providing a tubular device including a lubricious, hydrophilic, and/or otherwise coated inner surface.

34 Claims, 16 Drawing Sheets

U.S. PATENT DOCUMENTS

| | | | | |
|---|---|---|---|---|
| 4,478,898 | A | * 10/1984 | Kato | 428/36.91 |
| 4,516,972 | A | 5/1985 | Samson | |
| 4,636,346 | A | * 1/1987 | Gold et al. | 264/139 |
| 4,863,442 | A | 9/1989 | DeMello et al. | |
| 5,047,045 | A | * 9/1991 | Arney et al. | 606/194 |
| 5,176,661 | A | 1/1993 | Evard et al. | |
| 5,217,440 | A | * 6/1993 | Frassica | 604/524 |
| 5,254,107 | A | 10/1993 | Soltesz | |
| 5,370,655 | A | 12/1994 | Burns | |
| 5,400,785 | A | * 3/1995 | Crowley | 600/467 |
| 5,447,497 | A | 9/1995 | Sogard et al. | |
| 5,514,236 | A | 5/1996 | Avellanet et al. | |
| 5,549,109 | A | 8/1996 | Samson et al. | |
| 5,569,221 | A | * 10/1996 | Houser et al. | 604/524 |
| 5,676,659 | A | 10/1997 | McGurk | |
| 5,713,867 | A | 2/1998 | Morris | |
| 5,735,809 | A | 4/1998 | Gorsuch | |
| 5,811,043 | A | 9/1998 | Horrigan et al. | |
| 5,836,926 | A | 11/1998 | Peterson et al. | |
| 5,967,988 | A | 10/1999 | Briscoe et al. | |
| 6,004,310 | A | 12/1999 | Bardsley et al. | |
| 6,177,523 | B1 | 1/2001 | Reich et al. | |
| 6,183,443 | B1 | * 2/2001 | Kratoska et al. | 604/164.03 |
| 6,217,566 | B1 | * 4/2001 | Ju et al. | 604/526 |
| 6,310,244 | B1 | 10/2001 | Tran et al. | |
| 6,315,792 | B1 | 11/2001 | Armstrong et al. | |
| 6,511,462 | B1 | 1/2003 | Itou et al. | |
| 6,592,576 | B2 | 7/2003 | Andrews et al. | |
| 6,669,886 | B1 | 12/2003 | Willard | |
| 6,830,568 | B1 | 12/2004 | Kresten et al. | |
| 6,837,890 | B1 | 1/2005 | Chludzinski et al. | |
| 6,942,654 | B1 | 9/2005 | Schaefer et al. | |
| 6,945,970 | B2 | 9/2005 | Pepin | |
| 6,946,173 | B2 | 9/2005 | Lim et al. | |
| 6,979,290 | B2 | 12/2005 | Mourlas | |
| 7,188,623 | B2 | 3/2007 | Anderson et al. | |
| 7,273,469 | B1 | 9/2007 | Chan et al. | |
| 7,306,585 | B2 | * 12/2007 | Ross | 604/523 |
| 2001/0016702 | A1 | * 8/2001 | Benjamin | 604/19 |
| 2001/0053931 | A1 | * 12/2001 | Hess et al. | 623/1.15 |
| 2002/0156494 | A1 | 10/2002 | Simhambhatla et al. | |
| 2003/0233115 | A1 | 12/2003 | Eversull et al. | |
| 2004/0097788 | A1 | 5/2004 | Mourlas et al. | |
| 2005/0085841 | A1 | 4/2005 | Eversull et al. | |
| 2005/0085842 | A1 | 4/2005 | Eversull et al. | |
| 2005/0149104 | A1 | 7/2005 | Leeflang et al. | |
| 2005/0197623 | A1 | 9/2005 | Leeflang et al. | |
| 2005/0228452 | A1 | 10/2005 | Mourlas et al. | |
| 2007/0075452 | A1 | 4/2007 | Leeflang | |
| 2007/0088296 | A1 | 4/2007 | Leeflang | |

FOREIGN PATENT DOCUMENTS

| | | |
|---|---|---|
| WO | 9620750 | 7/1996 |
| WO | 9740880 | 11/1997 |
| WO | 9851370 | 11/1998 |
| WO | 9937350 | 7/1999 |
| WO | 0107101 | 2/2001 |
| WO | 03020353 | 3/2003 |
| WO | 2004075961 | 9/2004 |

OTHER PUBLICATIONS

PCT Written Opinion for PCT/US2006/039074, Applicant: ILH, LLC, Forms PCT/ISA/237, dated May 23, 2007, 13 pages.

Office Action for U.S. Appl. No. 11/341,324, May 28, 2008, 13 pages.

William A. English, Attorney for Applicant, Response to Office Action for U.S. Appl. No. 11/341,324, Oct. 28, 2008, 15 pages.

Office Action for U.S. Appl. No. 11/340,944, Sep. 30, 2008, 10 pages.

* cited by examiner

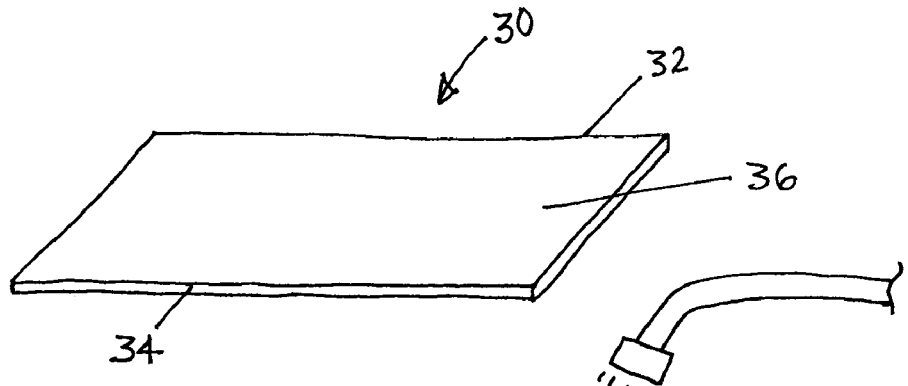
FIG. 2A
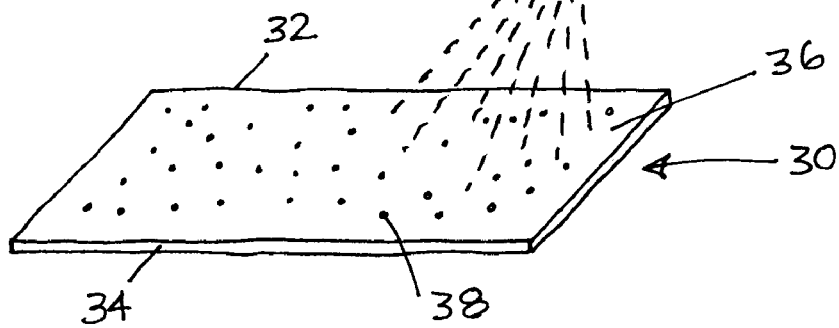
FIG. 2B
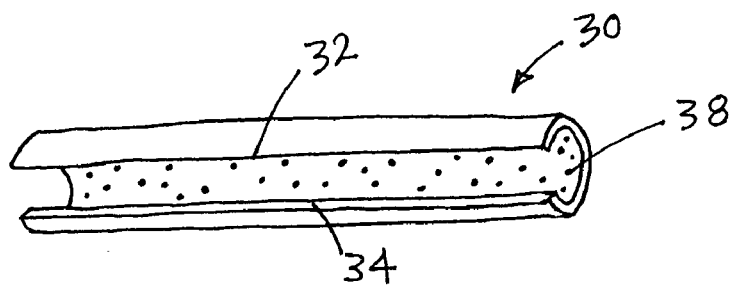
FIG. 2C
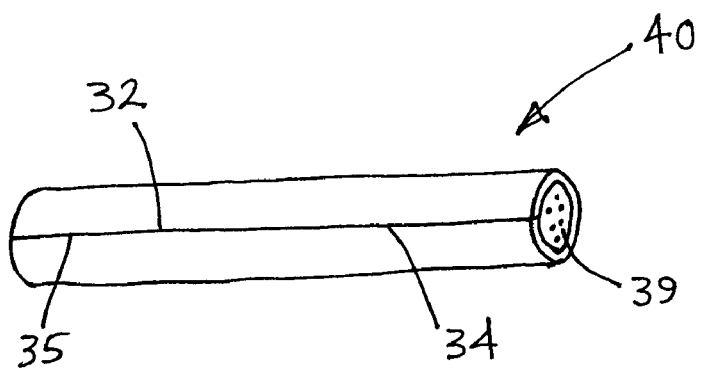
FIG. 2D
FIG. 2

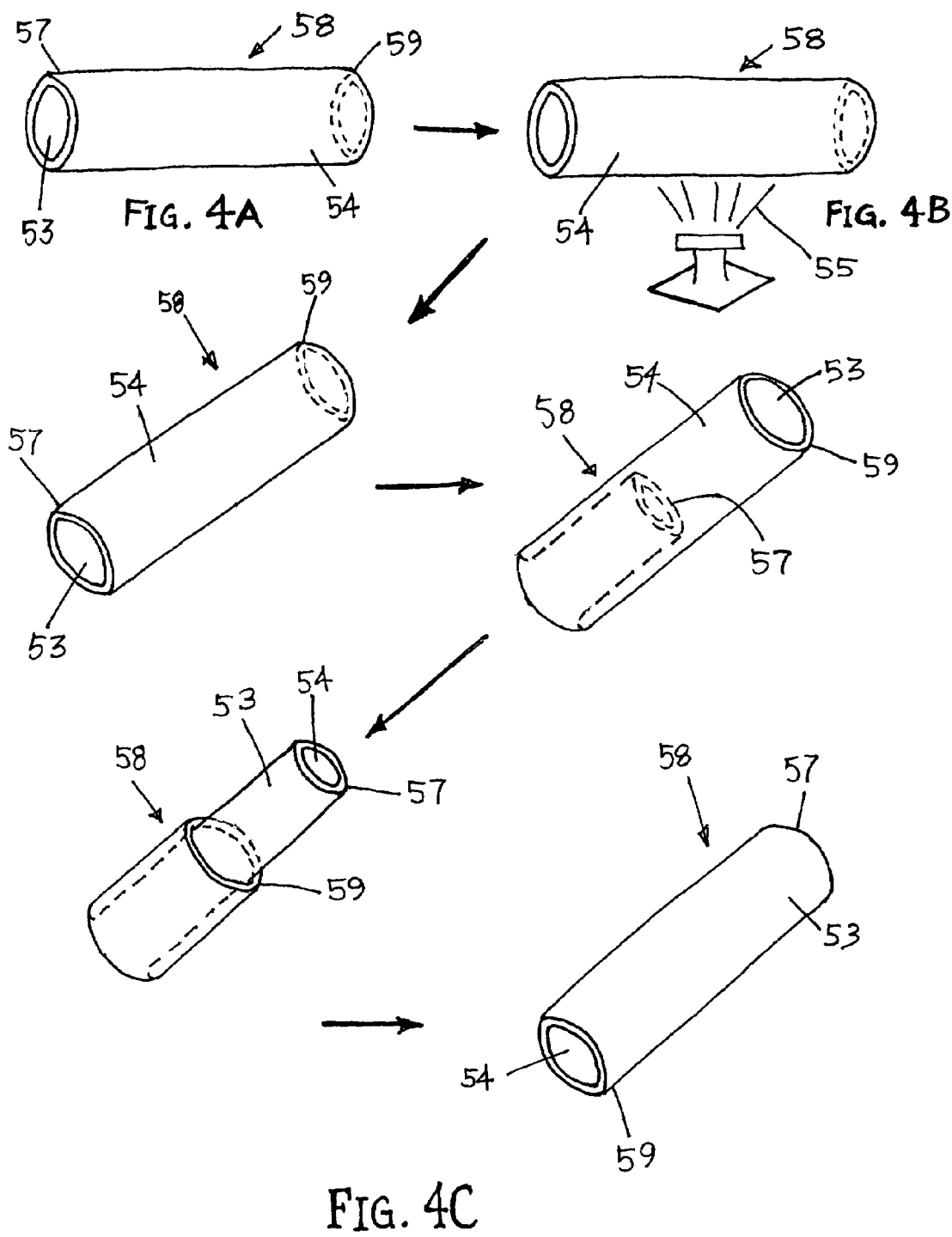

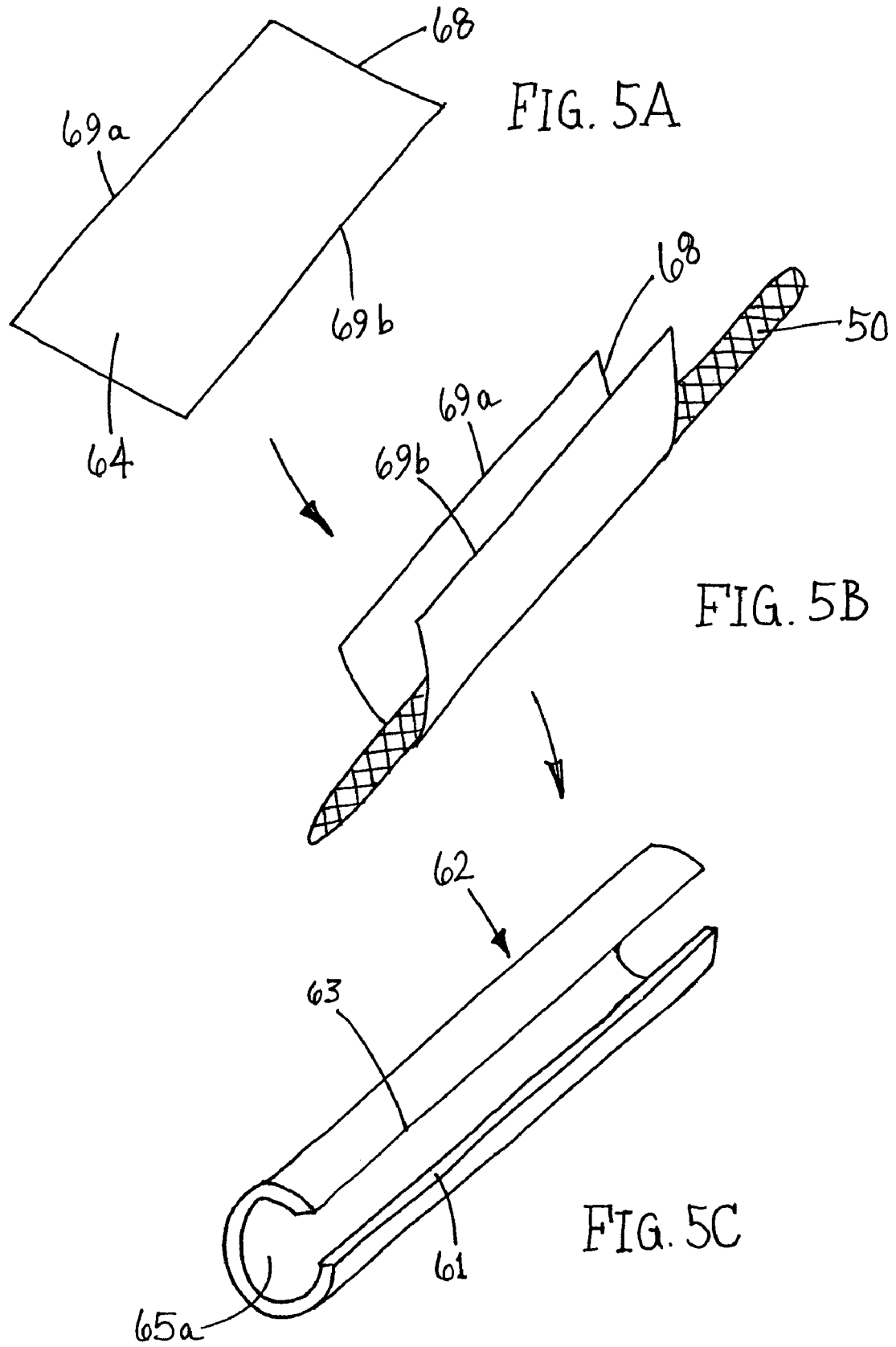

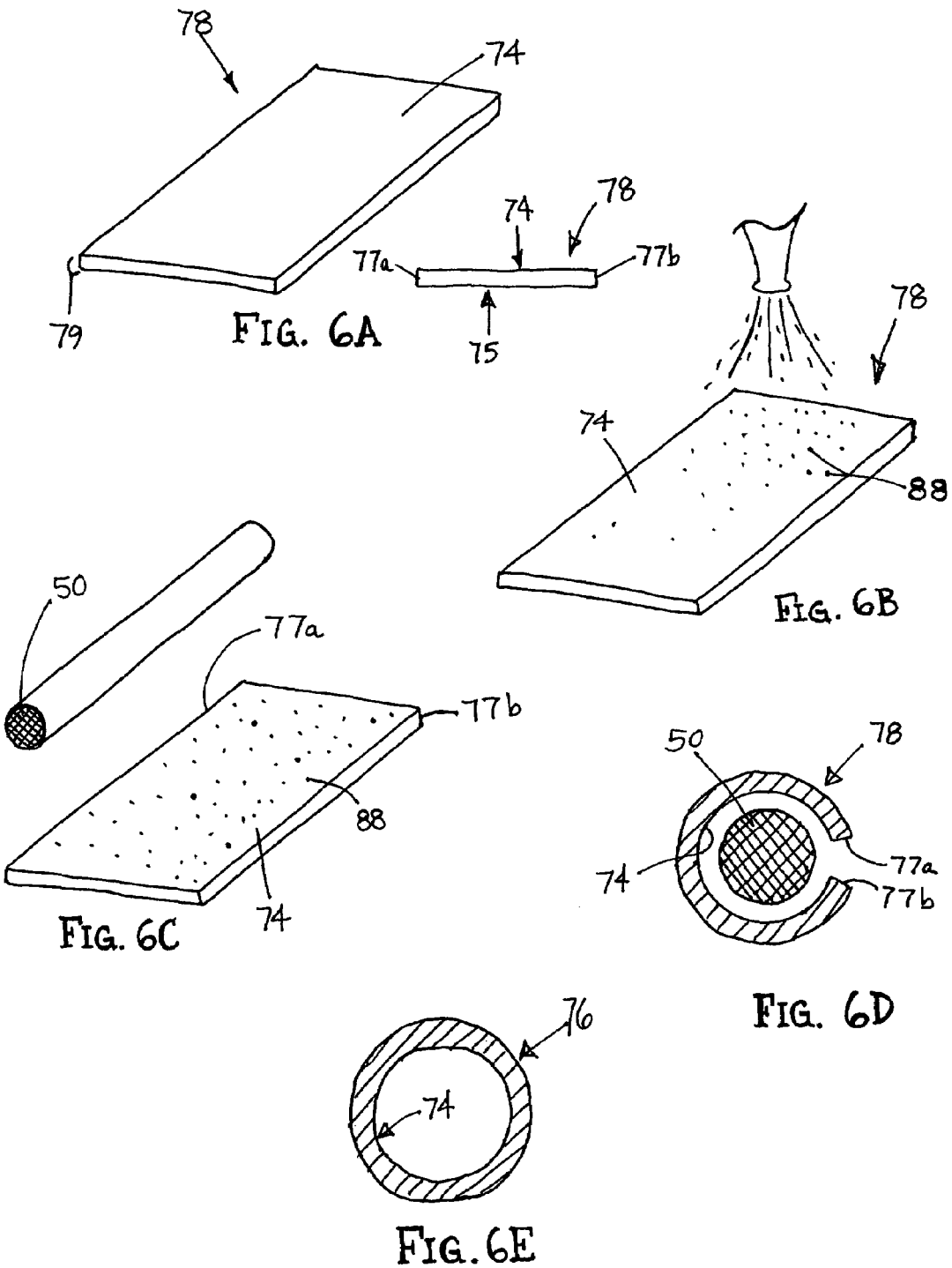

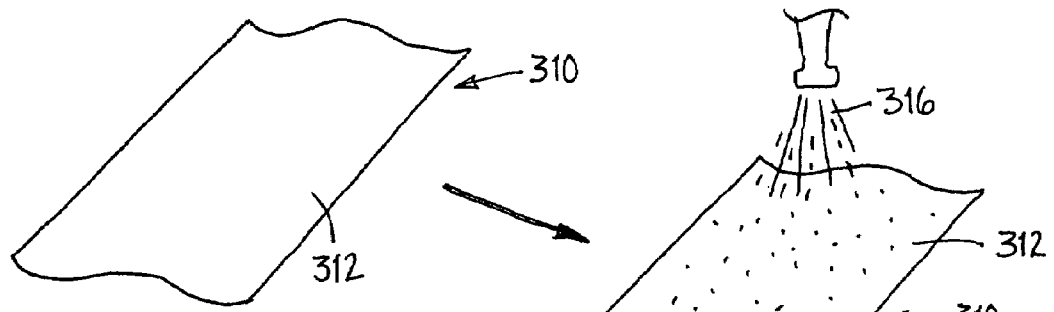
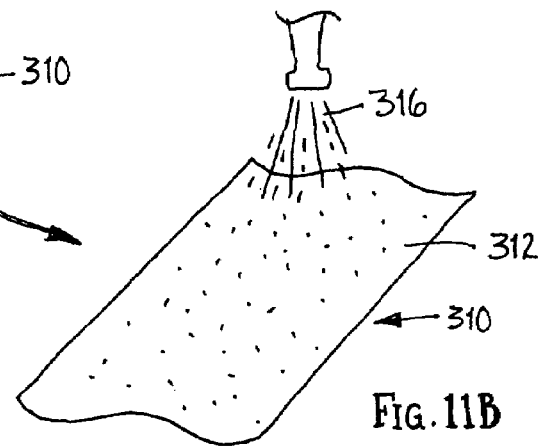
FIG. 11A
FIG. 11B
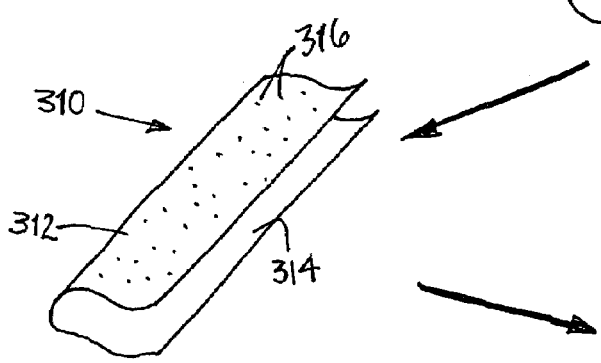
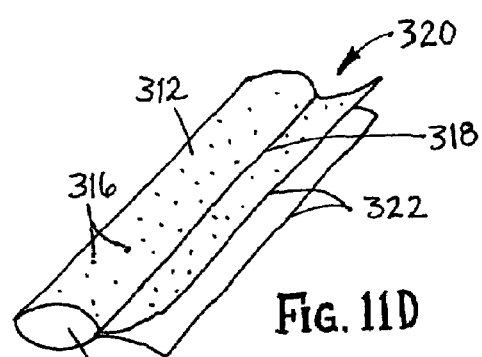
FIG. 11C
FIG. 11D
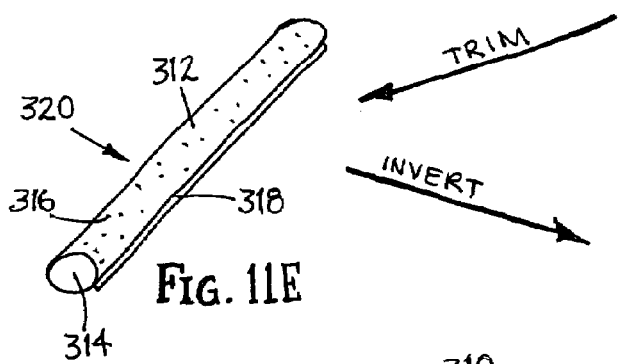
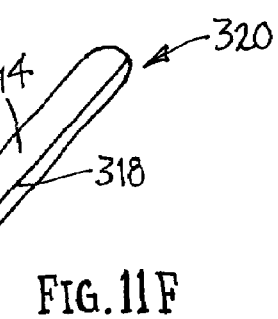
FIG. 11E
FIG. 11F
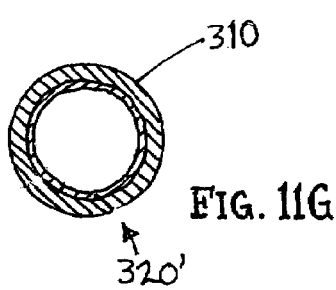
FIG. 11G

CATHETERS WITH LUBRICIOUS LININGS AND METHODS FOR MAKING AND USING THEM

This application claims benefit of provisional application Ser. No. 60/723,300, filed Oct. 4, 2005, the entire disclosure of which is expressly incorporated herein by reference.

FIELD OF THE INVENTION

The present invention relates generally to devices for providing access into body lumens and, more particularly, to catheters, sheaths, and other tubular devices with lubricious linings and methods for making and using them.

BACKGROUND

Catheters are elongate tubular devices sized for introduction into body passages and cavities of a patient, such as a patient's vascular system, gastrointestinal system, abdominal cavity, and the like. A catheter may include one or more lumens intended for passing various other devices, agents, and/or fluids into a body lumen or cavity accessed by the catheter. For such applications, the properties of the inner surface of one or more lumens may significantly impact the performance of the catheter. In particular, the lubricity of the inner surface may affect the ability to pass other devices, agents, and/or fluids through the lumen(s) of the catheter.

To enhance lubricity, it has been suggested to include polytetraflouroethylene ("PTFE"), polyethylene ("PE") or other cores surrounding the lumen of a catheter. The inner core may be intended to provide a lubricious inner surface to facilitate passing guidewires, pacing leads, or other devices through the lumen of the catheter. Constructing such a catheter, however, is complicated because of the difficulty bonding the inner core to the outer portions of the catheter.

For example, PTFE, in its native form is nearly impossible to bond; consequently, it must be held in place by mechanical interaction or must be etched in order to impart bondability. Further, because of the inaccessibility of the inner surface of the lumen of a catheter, mechanical abrasion or modification, cleaning, etching, application of adhesive, or other modifications of the inner surfaces to facilitate bonding are generally difficult to complete. PE, similar to PTFE, is also difficult to bond to other materials. In some cases, a third material must be used that is bondable both to PE and to other plastics. In both cases, the manufacturing process is complicated and the materials generally expensive.

Other methods for imparting lubricity to inner surfaces have been tried, for example, vapor deposition of surface coatings such as Paralene; however, this process is also complicated and does not result in optimal lubricity.

Hydrophilic coatings are well known and widely used in medical devices. These are readily applied to outer surfaces and frequently used on exteriors of catheters, for example, to facilitate tracking through the vasculature. Nevertheless, application of coatings to catheter exteriors is subject to process limitations. Furthermore, application of such coatings to inner surfaces is currently significantly hindered by technical challenges and therefore not practiced generally.

Hydrophilic coatings are generally dispersed within a solvent, for example, an aqueous or alcohol based solvent, which is applied to a surface and spread evenly in order to deposit a substantially uniform layer of dissolved hydrophilic coating on the surface after evaporation of the solvent. Given the appropriate processing equipment, techniques for coating exterior surfaces of catheters are known. Generally, this is accomplished by dipping. However, inner surfaces, especially small lumens of long catheters, are extremely difficult or impossible to coat because of the difficulty of evenly applying a solution to the inner surface.

For example, the size and geometry of an inner surface, e.g., a small round inner diameter of a catheter, may cause the solution to readily bead up rather than disperse evenly over the surface. Even if the solution could be evenly dispersed over the surface, for example, by addition of surfactants, evaporation of a solvent from inside a long small diameter tube may be slow and irregular, with likely condensation along the way. Thus, this method of coating an inner surface may not be feasible.

Furthermore, once the hydrophilic coating has been evenly deposited, it is often desirable to cross-link or otherwise increase the strength of adhesion of the coating, e.g., using heat or ultraviolet ("UV") light. In the case of UV light, it may be difficult to expose an inner surface of a catheter to UV light in order to cross-link the coating, unless the material being coated were transparent to UV light. Excessive exposure to UV light may also cause material degradation. Application of heat likewise is not always practicable as it may damage other device components.

With respect to coating outer surfaces, current methods make it relatively difficult to coat discrete sections without masking. Furthermore, the equipment and fixtures required for coating are generally expensive and processes may be difficult to control.

Due to these challenges, surface modification of inner surfaces, as for example, by application of hydrophilic, anti-antithrombotic, anti-biotic, drug-eluting, or other coatings is not easily accomplished, although it would be useful in a variety of applications. Furthermore, while coating outer surfaces is often performed, various limitations exist in current processes, which may be improved upon.

SUMMARY OF THE INVENTION

The present invention is directed generally to apparatus and methods for providing access to body lumens and/or for delivering instruments and/or agents into body lumens during a medical procedure. For example, in some embodiments, the present invention may provide simple and/or readily practicable methods for creating tubular devices having coated inner and/or outer surfaces. Furthermore, several devices are disclosed including coated inner and/or outer surfaces that provide one or more desired properties to the coated surfaces.

In accordance with one embodiment, a method is provided for making a tubular device. A thin sheet is coated on a first surface with a coating having one or more desired properties, e.g., a hydrophilic material having a predetermined lubricity. The sheet is rolled such that first and second side edges of the sheet are disposed adjacent one another and the coating is disposed inwardly. A longitudinal seam is created along the first and second side edge to create a sleeve.

A tubular structure is attached around the sleeve to create a tubular device. The sleeve and tubular structure may be attached together by at least one of laminating, bonding, and heat sealing. The tubular structure is generally attached in such a way as to substantially maintain the properties of the coated surface.

In an exemplary embodiment, the sleeve is positioned around a mandrel to create a first assembly, and the tubular structure is positioned over the first assembly to create a second assembly. Heat shrink tubing may be positioned over the second assembly, and heated to heat and/or compress the tubular structure. For example, the tubular structure may be heated sufficiently to cause the tubular structure to at least partially reflow to bond or laminate the tubular structure around the sleeve. After sufficient heating, the shrink tubing may be removed from around the second assembly, and the mandrel removed to create the tubular device. Alternatively, the tubular structure, thin sheet, and mandrel may be directed through a heated die to attach the tubular structure to the thin sheet.

In accordance with another embodiment, a method is provided for making a tubular device that includes coating a first surface of a thin sheet with a coating imparting one or more desired properties to the first surface. The thin sheet may be wrapped at least partially around a mandrel with the first surface disposed inwardly. A slotted tube may be positioned around the thin sheet and mandrel, and attached to the thin sheet to form a tubular structure.

In an exemplary embodiment, the thin sheet is wrapped only partially around. the mandrel such that excess edges of the thin sheet are disposed adjacent one another away from the mandrel. After the slotted tube is attached to the thin sheet, excess edges of the thin sheet may be trimmed from the tubular structure.

In another embodiment, the slotted tube includes longitudinal edges defining a slot, and the slotted tube may be positioned around the thin sheet and mandrel by separating the longitudinal edges. The longitudinal edges may be bonded together when the slotted tube is attached to the thin sheet, e.g., by reflowing or otherwise heating material of the slotted tube.

In accordance with still another embodiment, a method is provided for making a tubular device that includes providing a thin sleeve including an outer first surface and an inner second surface, coating the first surface with a coating to impart the first surface with one or more desired properties, and inverting the thin sleeve such that the first surface defines an inner surface of the inverted sleeve and the second surface defines an outer surface of the inverted sleeve.

Optionally, a tubular structure may be attached around the inverted sleeve, thereby providing a tubular device including an inner surface with the one or more desired properties.

In accordance with yet another embodiment, a method is provided for making a tubular device sized for introduction into a body lumen that includes providing a sheet of material comprising a first surface and a second surface, coating the first surface of the sheet with a coating, rolling the sheet until longitudinal edges of the sheet are disposed adjacent one another, and attaching the longitudinal edges to one another to form a continuous wall defining a lumen.

In exemplary embodiments, the longitudinal edges may be attached to one another by using at least one of heat bonding, an adhesive, and/or lamination.

In accordance with yet another embodiment, a tubular device is provided that includes a proximal end, a distal end sized for introduction into a body lumen, and a lumen extending between the proximal and distal ends. In one embodiment, the tubular device may include an inner polyurethane liner including a coating on an inner surface thereof, and an outer layer, e.g., including PEBAX, nylon, and/or urethane. For example, the tubular device may be a delivery sheath, which may include a braid surrounding at least a portion of the liner. In another example, the tubular device may be a core for a guidewire lumen. In yet another example, the polyurethane liner may be Ether-based or Esther-based, the latter of which may improve cross linking and/or adhesion of the coating.

In accordance with still another embodiment, a lead is provided that includes a proximal end, a distal end sized for introduction into a body lumen and at least one electrode on the distal end. The lead may include a lead body having an outer surface extending between the proximal and distal ends, and a polyurethane cover surrounding at least a portion of the outer surface. The cover may include a coating imparting one or more predetermined properties to the portion of the outer surface, e.g., including a lubricious and/or hydrophilic material. Optionally, the cover may be removable from around the lead body.

Other aspects and features of the present invention will become apparent from consideration of the following description taken in conjunction with the accompanying drawings.

BRIEF DESCRIPTION OF THE DRAWINGS

FIGS. 2A-2D show a first method for making a thin-walled sleeve. FIGS. 2A and 2B are perspective views of a thin film sheet being coated, and FIGS. 2C and 2D are perspective views showing the coated sheet being rolled to create the thin-walled sleeve.

FIGS. 4A-4C are perspective views, showing a method for coating and inverting a thin-walled sleeve.

FIGS. 5A-5C are perspective views and FIGS. 5D-5F are cross-sectional views, showing another method for making a tubular device including a coated inner surface.

FIGS. 6A-6C are perspective views and FIGS. 6D and 6E are cross-sectional views, showing yet another method for making a tubular device including a coated inner surface.

FIGS. 11A-F are perspective views and FIG. 11G is a cross-sectional view, showing another method for making a tubular device including a coated inner surface.

DETAILED DESCRIPTION OF THE PREFERRED EMBODIMENTS

Figure 1A:
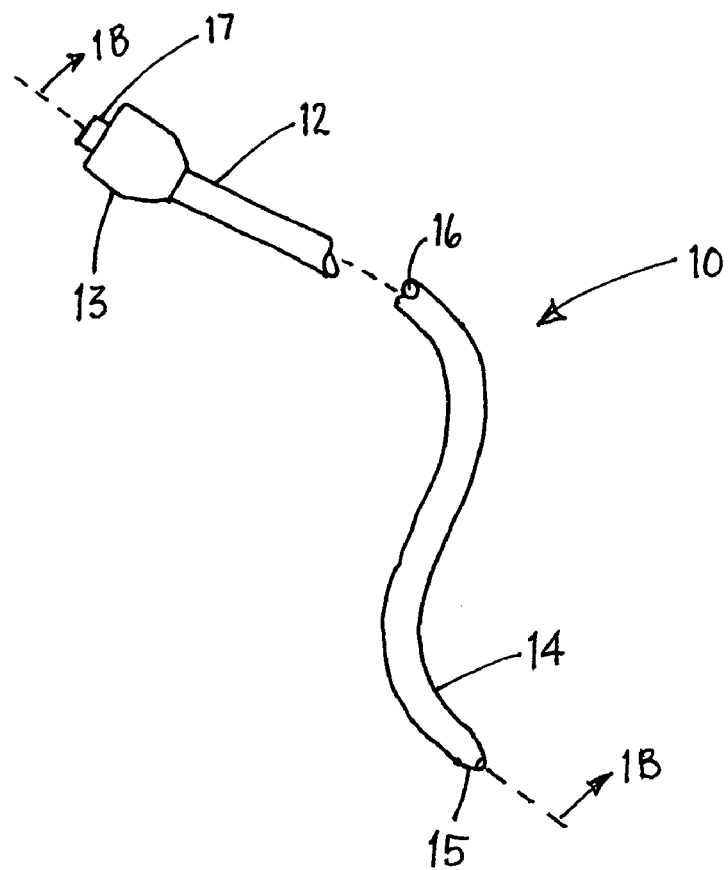
FIG. 1A is a perspective view of an exemplary embodiment of a tubular device, including a lumen extending between proximal and distal ends thereof.
Figure 1B:
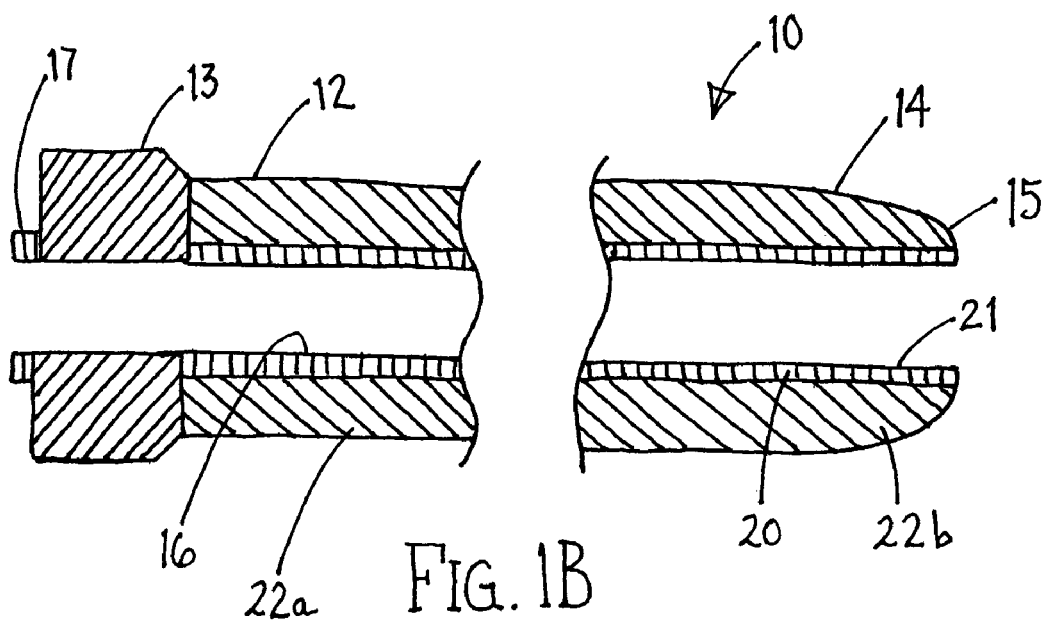
FIG. 1B is a cross-sectional view of the tubular device of FIG. 1A, taken along line 1B-1B, showing a coated liner surrounding the lumen and an outer layer surrounding the coated liner.

Turning to the drawings, FIGS. 1A and 1B show an exemplary embodiment of an apparatus 10 for accessing a body lumen (not shown) and/or for delivering one or more fluids, agents, and/or instruments (also not shown) within a body lumen. In exemplary embodiments, the apparatus 10 may be a guide catheter, a procedure catheter, a sheath, an imaging device, or other tubular device sized for introduction into a body lumen, such as a vessel within a patient's vasculature, a passage within a patient's gastrointestinal tract, urogenital tract, reproductive tract, respiratory tract, lymphatic system, and the like, as described further below.

Generally, the apparatus 10 is an elongate tubular member including a proximal end 12, a distal end 14 sized for insertion into a body lumen, and a lumen 16 extending between the proximal and distal ends 12, 14. Optionally, the apparatus 10 may include one or more additional lumens (not shown), which may be disposed concentrically around or side-by-side with the lumen 16. The lumen 16 may be sized for receiving a guide wire, procedure catheter, cardiac lead, needle, or other instrument (not shown), and/or for delivering fluids or other flowable agents or materials therethrough.

Optionally, the distal end 14 may include a tapered, rounded, or otherwise shaped distal tip 15, e.g., to provide a substantially atraumatic tip and/or facilitate advancement or navigation through various anatomy. In addition or alternatively, the distal end 14 may include one or more therapeutic and/or diagnostic elements, e.g., one or more balloons, stents, sensors, electrodes, steering mechanisms, imaging devices, needles, and the like (not shown), depending upon the particular intended application for the apparatus 10.

Optionally, the proximal end 12 may include a handle 13 and/or one or more ports, e.g., port 17 communicating with the lumen 16. In addition or alternatively, the handle 13 and/or proximal end 12 may include one or more connectors, such as luer lock connectors, electrical connectors, and the like, for connecting other devices (not shown) to the apparatus 10, such as syringes, displays, controllers, and the like (also not shown). In addition, the handle 13 may include one or more actuators, such as sliders, buttons, switches, and the like, e.g., for activating and/or manipulating components (also not shown) on the distal end 14 or otherwise operating the apparatus 10.

With particular reference to FIG. 1B, the apparatus 10 generally includes an inner liner 20 surrounding the lumen 16 and an outer layer 22 surrounding the inner liner 20. The inner liner 20 may include a relatively thin film, sheet, or other material including an inner surface 21. The inner surface 21 may include a coating having one or more desired properties, e.g., a predetermined lubricity, hydrophilic characteristic, and the like. The outer layer 22 may be attached to the inner layer 20, e.g., by laminating, adhering, adhesive bonding, ultrasonic welding, reflowing or other heating, and the like, as described elsewhere herein.

Optionally, the outer layer 22 may include one or more sublayers (not shown). For example, the outer layer 22 may include a braided or helical reinforcing layer (not shown) surrounding the inner layer 20 and one or more tubular layers (also not shown) surrounding the reinforcing layer and/or between the reinforcing layer and the inner layer 20. In exemplary embodiments, the reinforcing layer may include one-or more round or flat wires, filaments, strands, and the like, e.g., formed from metal, such as stainless steel, plastic, woven fibers, such as glass, Kevlar, and the like, or composite materials. Materials that may be used in the outer layer 22 include PEBAX, urethane, FEP, PFA, polyethylene ("PE"), polyamide (Nylon), silicone, polypropylene, polysulfone, polyvinylchloride (PVC), polystyrene, polycarbonate, polymethylmethacrylate, and the like. Materials may be primarily selected for optimal mechanical, bonding, and/or other properties and subsequently imparted with desired surface properties, for example lubricity, by coating.

Exemplary outer layers that may be included in the apparatus 10 and methods for making them are disclosed in U.S. Pat. Nos. 4,478,898, 4,863,442, 5,217,440, 5,254,107, 5,676, 659, 5,811,043, 5,836,926, 6,004,310, 6,669,886, 6,837,890, and 6,945,970. The entire disclosures of these references are expressly incorporated by reference herein.

The outer layer 22 may have a substantially homogenous construction between the proximal and distal ends 12, 14. Alternatively, the construction may vary along the length of the apparatus 10 to provide desired properties. For example, the outer layer 22a at or adjacent the proximal end 12 may be substantially rigid or semi-rigid, e.g., providing sufficient column strength to allow the apparatus 10 to be pushed from the proximal end 12. In addition, the reinforcing layer or other material in the outer layer 22 may allow the apparatus 10 to be twisted from the proximal end 12, e.g., to rotate the distal end 14 within a patient's body. Thus, the distal end 14 of the apparatus 10 may be manipulated within a patient's body from the proximal end 12 without substantial risk of buckling and/or kinking. Optionally, the outer layer 22b at or adjacent the distal end 14 may be substantially flexible or semi-rigid, e.g., to allow the distal end 14 to bend easily or otherwise be advanced through tortuous anatomy and/or provide a substantially atraumatic distal tip 15. Furthermore, the outer layer 22a, may have one or more transition regions along its length, transitioning from one desired construction to another.

In exemplary embodiments, the apparatus 10 may have an outer diameter between about half and twenty millimeters (0.5-20 mm), and a length between about five and one hundred fifty centimeters (5-150 cm). The inner liner 20 may have a wall thickness between about 0.0001-0.01 inch (0.0025-0.25 mm) and the outer layer 22 may have a wall thickness between about 0.0005-0.2 inch (0.0127-5.08 mm).

Turning to FIGS. 2A-2D and 3A-3E, a first exemplary method is shown for making a tubular device, such as apparatus 10 described above. Initially, as shown in FIG. 2A, a thin film sheet 30 may be provided including a first side edge 32 and a second side edge 34 opposite one another, and a first upper surface 36 and a second lower surface (not shown). The sheet 30 may be formed from a single layer or multiple layers of material. In an exemplary embodiment, the sheet 30 may be formed from a sheet of polyurethane, e.g., having a thickness between about 0.0001-0.01 inch (0.0025-0.25 mm). For example, the polyurethane may be Ether-based or Ester-based. However, other suitable polymers may also be used, such as polyolefin, PEBAX, nylon, silicone, polypropylene, and polyethylene.

With the sheet 30 substantially flat, a coating 38 is applied to the first surface 36. Alternatively, the sheet 30 may be disposed in a concave, convex, or other nonplanar configuration (not shown), as long as the first surface 36 is readily accessible. In an exemplary embodiment, the coating includes a hydrophilic material, such as Polyvinylpyrrolidone, and is sprayed onto the first surface 36 to apply a substantially uniform thickness coating.

Alternatively, the coating may be applied using other procedures, such as rolling, brushing, spreading by maer rods, or dipping, e.g., to provide a substantially uniform thickness coating 38 on the first surface 36. The hydrophilic material may provide a predetermined lubricity on the first surface 36. Alternatively, other materials may be applied to provide one or more desired properties on the first surface 36, e.g. anti-thrombotic or anti-hemolytic materials, drug-eluting coatings, and the like.

Turning to FIG. 2C, the sheet 30 may be rolled such that the first and second side edges 32, 34 are disposed adjacent one another and the first upper surface 36 is now disposed inwardly. The first and second side edges 32, 34 may then be attached to one another to create a relatively thin-walled sleeve 40.

In an exemplary embodiment, the side edges 32, 34 may be lapped against one another along the uncoated surface or the side edges 32, 34 may be butted against one another. The side edges 32, 34 may then be attached to one another to create a longitudinal seam 35, as shown in FIG. 2D. Optionally, the sheet 30 may be wrapped around a mandrel (not shown), which may facilitate attaching the side edges 32, 34 and/or facilitate maintaining a desired inner diameter for the sleeve 40.

In these configurations, the coating 38 may not interfere with attaching the side edges 32, 34 together, because the contact surface between the side edges 32, 34 is uncoated. In exemplary embodiments, the side edges 32, 34 are attached to one another by heat bonding, i.e., heating to fuse the side edges 32, 34 together, using ultrasonic energy, and/or using one or more adhesives. The resulting device is a relatively thin-walled sleeve 40 including a lumen 39 having an inner surface coated, as shown in FIG. 2D. Optionally, if any excess material remains between the side edges 32, 34 and the longitudinal seam, the excess material may be cut away or otherwise removed from the thin-walled sleeve 40.

Turning to FIGS. 3A-3E, the thin-walled sleeve 40 may be incorporated into a catheter or other tubular device, similar to the apparatus 10 described above. It will be noted that annular spaces are shown between the various layers or components shown in the drawings. These spaces are not to scale but are shown merely to clarify the various components. It will be appreciated that the spaces may be relatively small or adjacent components may directly contact one another such that there is little or substantially no space between the contacting components or layers.

Figure 3A:
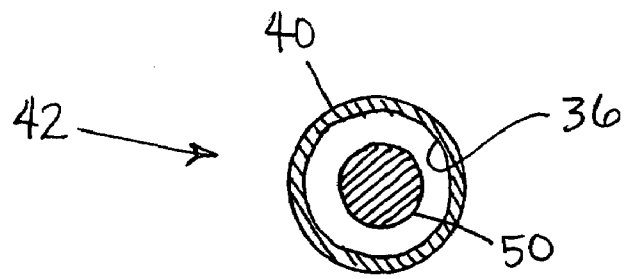
FIGS. 3A-3E are cross-sectional views, showing a method for making a tubular device including a thin-walled sleeve.

For example, as shown in FIG. 3A, the thin-walled sleeve 40 may be positioned around a mandrel 50, thus creating a first assembly 42. The mandrel 50 may be an elongate cylindrical structure, e.g., a tube or rod, formed from material able to withstand the parameters used during assembly, e.g., elevated temperatures used to heat the materials during assembly. The thin-walled sleeve 40 may fit relatively snugly around the mandrel 50 such that the inner surface 36 is substantially smooth, e.g., without substantial wrinkles or other irregularities.

The mandrel 50 may be formed from or coated with a lubricious, hydrophilic, or other material that is non-bondable to the thin-walled sleeve 40. Exemplary materials for the mandrel 50 may include metal, such as stainless steel, coated stainless steel, NiTi alloy, MP35N, Elgiloy, and the like. Alternatively, plastic, such as Teflon, composite, or non-metallic materials may be used.

Figure 3B:
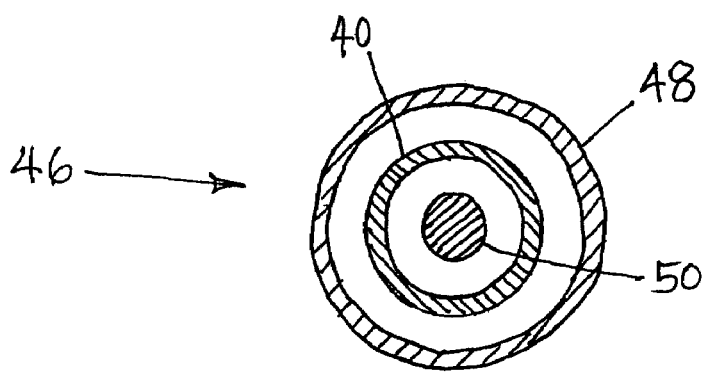

Turning to FIG. 3B, a tubular structure 48 is then positioned over the first assembly 42, creating a second assembly 46. In an exemplary embodiment, the tubular structure 48 may be an extrusion of PEBAX, nylon, polyimide, HDPE, Plexar, and/or Urethane having an inner diameter sized to slide around the thin-walled sleeve 40. Alternatively, other suitable materials described herein may also be employed, such as the multiple sublayer outer layers described above.

Generally, the tubular structure 48 may have a thickness that is substantially greater than a thickness of the thin-walled sleeve 40. Thus, the tubular structure 48 may provide the desired structural integrity of the final apparatus being constructed. Nevertheless, the material of the thin-walled sleeve may also be selected based on desired mechanical or structural properties and desired surface properties subsequently imparted by coating. In exemplary embodiments, the tubular structure 48 may be extruded or otherwise flowed around the thin-walled sleeve 40, or may be preformed and then threaded or otherwise advanced over the thin-walled sleeve 40. Alternatively, the tubular structure 48 may be built up around the thin-walled sleeve 40, e.g., by applying one or more successive layers around the thin-walled sleeve 40 until a desired outer layer is obtained.

Figure 3C:
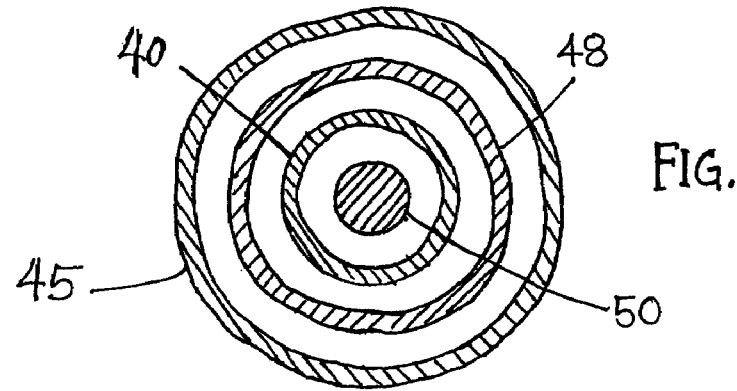

Turning to FIG. 3C, heat shrink tubing 45 may be positioned over the second assembly 46, and then heat may be applied to the heat shrink tubing 45, e.g., sufficient to cause the shrink tubing 45 to shrink around the second assembly 46. The combination of heat and inward compression may cause the tubular structure 48 to at least partially melt or otherwise reflow around the thin-walled sleeve 40, thereby fusing the tubular structure 48 to the thin-walled sleeve 40. For example, hot air may be blown around the shrink tubing 45 or the entire assembly may be placed in an oven, creating sufficient heat to cause the shrink tubing 45 to constrict around the tubular structure 48.

Figure 3D:
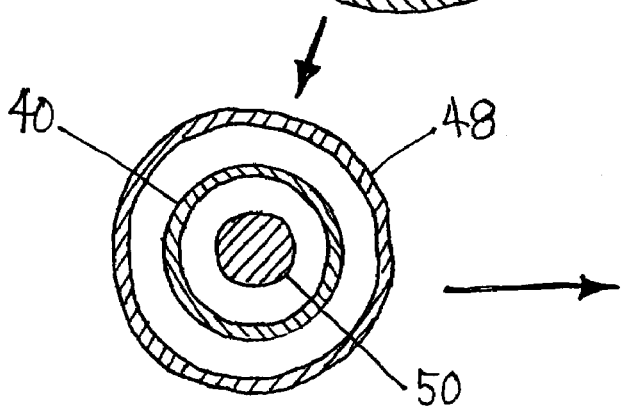
Figure 3E:
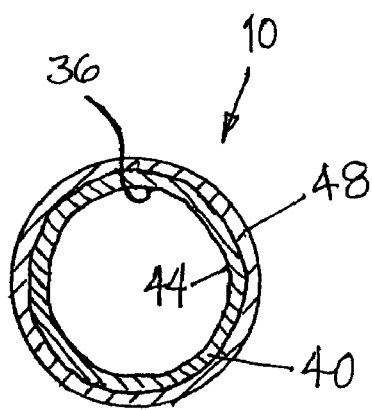

As shown in FIG. 3D, the shrink tubing 45 may then be removed from the second assembly 46. For example, the shrink tubing 45 may be formed from a material that may be torn easily. In addition or alternatively, the shrink tubing 45 may include one or more weakened seams, tabs, and the like (not shown) to facilitate removing the shrink tubing from around the second assembly 46. Alternatively, the shrink tubing 45 may be rolled, slid, or otherwise removed from one end of the tubular structure 48. As seen in FIG. 3E, the mandrel 50 may be removed from within the thin-walled sleeve 40 either before or after removing the shrink tubing 45.

The result is a tubular device that includes an outer layer 48, and a lumen 44 including a coated inner surface. Optionally, one or more additional components may be added to the tubular device, such as a handle and/or one or more therapeutic and/or diagnostic elements, as described above.

Figure 4D:
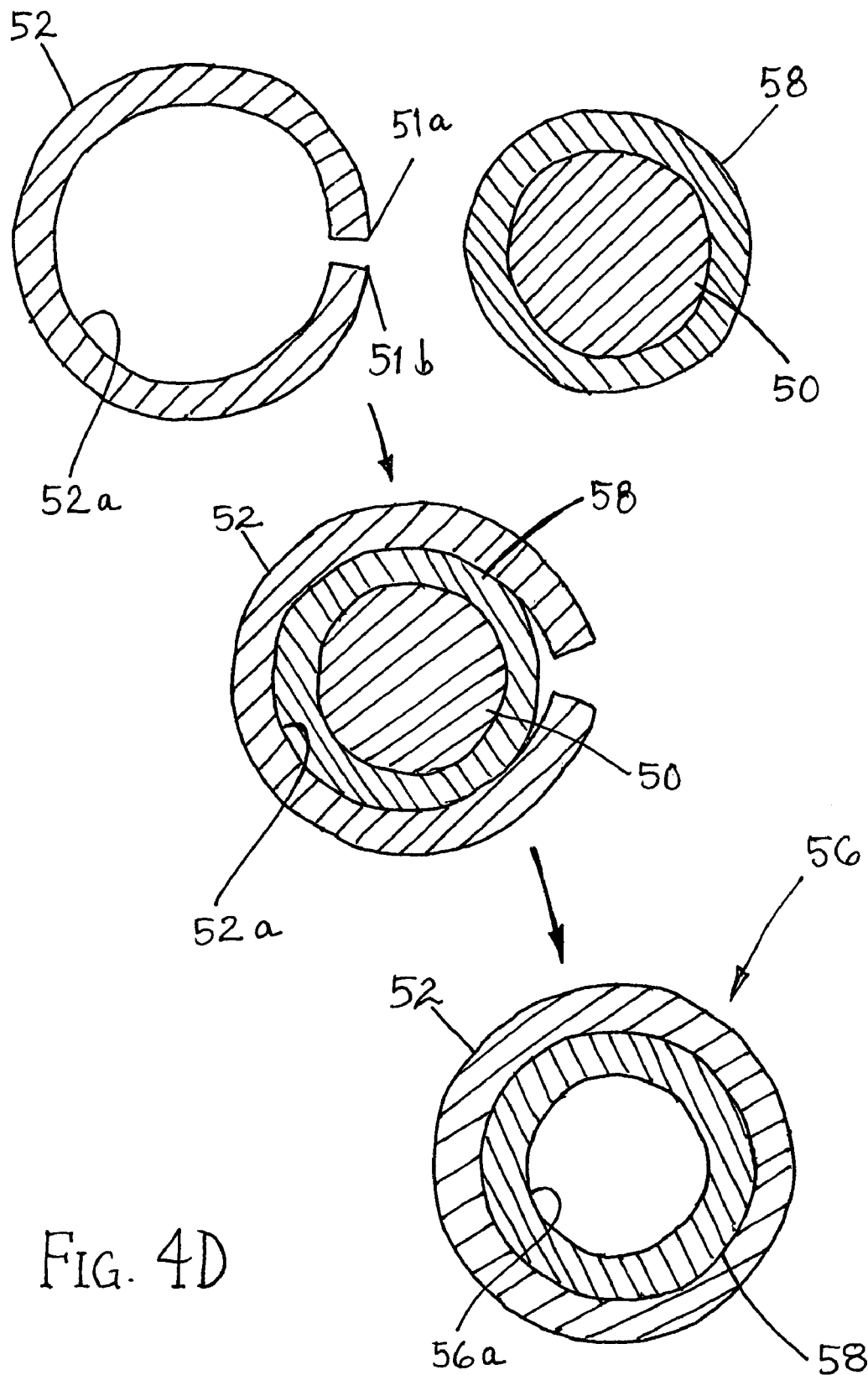
FIG. 4D is a cross-sectional view and FIGS. 4E-4G are perspective views, showing a method for making a tubular device including a thin-walled sleeve.

Turning to FIGS. 4A-4G, another method is shown for making a tubular device, such as apparatus 10 described above. As shown in FIG. 4A, a relatively thin-walled sleeve 58 may be provided that initially includes first and second ends 57, 59 defining an outer surface 54 and an inner surface 53 extending therebetween. The thin-walled sleeve 58 may include a tube of thin-walled material including one or more layers, similar to the sheet described above. The thin-walled sleeve 58 may be formed from continuous extrusion, injection molding, blow molding, and the like. Alternatively, the sleeve 58 may be formed from a sheet that is rolled and has its longitudinal edges sealed or otherwise bonded (similar to the method described above, but without coating).

In FIG. 4B, the thin-walled sleeve 58 is coated on the outer surface 54. For example, a desired liquid material 55 may be sprayed or brushed onto the outer surface 54, e.g., to provide a substantially uniform thickness hydrophilic or other coating on the outer surface 54. Alternatively, the coating may be applied by dipping the thin-walled sleeve 48 in a desired solution, e.g., a hydrophilic composition. In other alternatives plasma deposition, electrostatic. deposition, vapor deposition, and the like may be used. If desired, the thin-walled sleeve may be positioned over a mandrel (not shown), pressurized, or otherwise supported to facilitate application of a desired liquid, solution, and/or coating.

Referring to FIG. 4C, the coated thin-walled sleeve 58 is then inverted so that the coated outer surface 54 and the inner surface 53 are now arranged on the interior and exterior of thin film sleeve 58, respectively. For example, the first end 57 of the thin-walled sleeve 58 may be pulled inwardly through the thin-walled sleeve 58 and out the second end 59. Thus, the coated surface now occupies the interior of the thin-walled sleeve 58.

Turning to FIG. 4D, a tubular structure 52 may then be attached to or around the inverted thin-walled sleeve 58 to provide a tubular device 56. Similar to the previous embodiments, the inverted thin-walled sleeve 58 may be positioned over a mandrel 50. The tubular structure 52 may then be positioned over the inverted thin-walled sleeve 58, thereby capturing the thin-walled sleeve 58 within the lumen 52a.

In the embodiment shown in FIG. 4D, the tubular structure 52 may be a slotted tube defining a lumen 52a, and including longitudinal edges 51a, 51b defining a slot therebetween that communicates with the lumen 52a. The tubular structure 52 may be formed from one or more layers, as described elsewhere herein. The tubular structure 52 may be formed as a generally "C" shaped cross-section, e.g., by extrusion, injection molding, lay-up, and the like. Alternatively, the tubular structure 52 may be formed as a continuous-walled tube, which may be slit or otherwise cut to create the slot and the longitudinal edges 51a, 51b.

To position the tubular structure 52 around the inverted thin-walled sleeve 58, the longitudinal edges 51a, 51b may be separated away from one another sufficient distance to allow the mandrel 50 and thin-walled sleeve 58 thereon to pass between the longitudinal edges 51a, 51b and enter the lumen 52a. In one embodiment, the diameter of the lumen 52a may be slightly smaller than the outer diameter of the thin-walled sleeve 58 on the mandrel 50. This embodiment may ensure that the tubular structure 52 is fitted snugly around the thin-walled sleeve 58.

The tubular structure 52 and the inverted thin-walled sleeve 58 may then be bonded or otherwise attached to one another. For example, similar to the previous embodiment, heat shrink tubing (not shown) may be positioned around the tubular structure 52 and heated to cause the shrink tubing to heat and/or compress radially inwardly the tubular structure 52. Alternatively, the entire assembly may be directed through a heated die.

This may cause the tubular structure 52 to at least partially melt or reflow, thereby fusing or otherwise bonding the longitudinal edges 51a, 51b together to provide a continuous wall. In addition, the heating may reflow, fuse, or otherwise bond the inverted thin-walled sleeve 58 to the inner surface of the tubular structure 52. Optionally, other processes may be used, such as delivering ultrasonic energy, lamination, and/or applying adhesives to attach the tubular structure 52 around the inverted thin-walled sleeve 58.

As shown in FIG. 4D, the resulting tubular device 56 (having lubricious inner surface 56a) is removed from the mandrel 50. Optionally, other components (not shown) may be added to the tubular device 56, as described elsewhere herein.

Figure 4E:
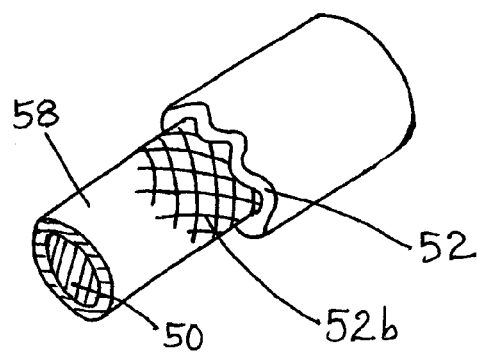

Turning to FIG. 4E, another method is shown for attaching a tubular structure 52 over the inverted thin-walled sleeve 58. After positioning the inverted thin-walled sleeve 58 around a mandrel 50, a reinforcement layer 52b may be applied around the inverted thin-walled sleeve 58. For example, one or more wires, filaments, or other strands may be wound or otherwise positioned around the inverted thin-walled sleeve 58, e.g., in a braided pattern (shown in FIG. 4E) or in a helical pattern (not shown).

A tubular structure 52 may then be applied around the reinforcement layer 52b. The tubular structure 52 may include one or more layers applied successively around the reinforcing layer 52b. For example, filament wound fibers and polymeric material (not shown) may be wound around the reinforcing layer 52b or thermoplastic or other flowable material may be extruded or otherwise directed around the reinforcing layer 52b.

Figure 4F:
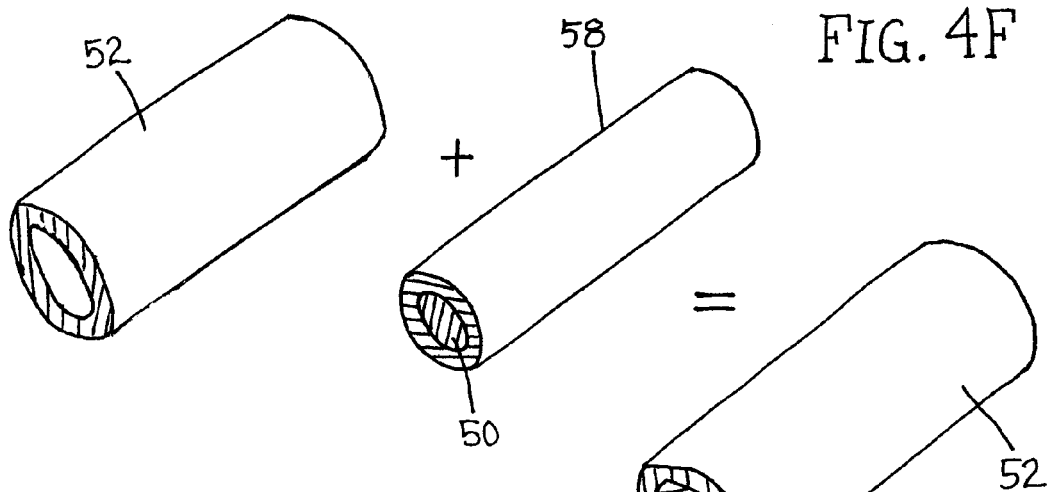
Figure 4G:
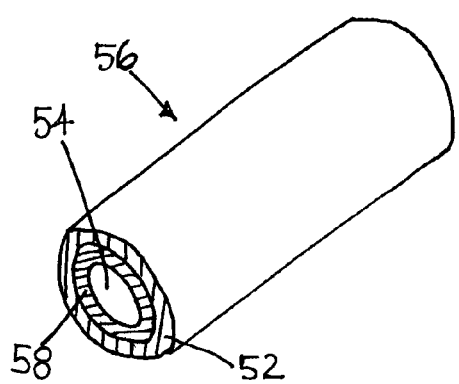

Turning to FIG. 4F, an alternative method is shown for attaching the tubular structure 52 around the inverted thin-walled sleeve 58. In this embodiment, the tubular structure 52 is a completely formed tube that may be positioned over and bonded to the inverted thin-walled sleeve 58. For example, an adhesive may be applied around the inverted thin-walled sleeve 58, and the tubular structure 52 may be advanced over the adhesive. The adhesive may then be cured, e.g., by heating, pressure, ultraviolet light exposure, and/or allowing sufficient time to cure. The mandrel 50 may then be removed, e.g., to provide the tubular device 56 shown in FIG. 4G.

Turning to FIG. 5A-5F, still another method is shown for making a tubular device, such as apparatus 10 described above. As shown FIG. 5A, a thin-walled sheet 68 may be provided that includes a first upper surface 64, a second lower surface (not shown), and opposing longitudinal edges 69a, 69b. The thin-walled sheet 68 may comprise materials and configurations, similar to other embodiments described elsewhere herein.

The first surface 64 of the thin-walled sheet 68 is coated, as described elsewhere herein, to provide a desired coating having one or more desired properties on the first surface 64. In an exemplary embodiment, the one or more desired properties includes a predetermined lubricity on the first surface 64, e.g., provided by a hydrophilic coating, such as those described elsewhere herein.

Turning to FIG. 5B, the thin-walled sheet 68 is partially wrapped around a mandrel 50 (which may be similar to other embodiments described herein) such that the first surface 64 is disposed inwardly towards the mandrel 50. As shown in FIG. 5C, a slotted tube 62 may be provided that may be formed similar to the embodiments described elsewhere herein. Thus, the slotted tube 62 may include opposing longitudinal edges 61, 63 defining a slot communicating with a lumen 65 of the slotted tube 62.

Figure 5D:
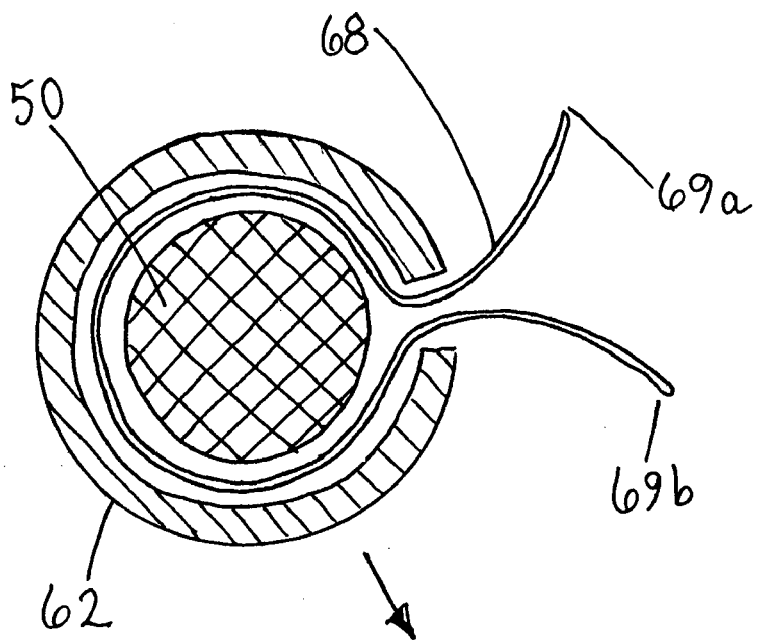

Turning to FIG. 5D, the slotted tube 62 may be positioned around the thin-walled sheet 68 by separating the longitudinal edges 61, 63 sufficiently to insert the mandrel 50 and thin-walled sheet 68 through the slot and into the lumen 65. As shown, the longitudinal edges 69a, 69b of the thin-walled sheet 68 may extend out from between the longitudinal edges 61, 63 of the slotted tube 62.

The slotted tube 62 may then be attached to the thin-walled sheet 68, e.g., by heat-sealing, advancement through a heated die or other lamination, bonding, and the like, as described elsewhere herein. For example, heating of the assembly may cause the material of the slotted tube 62 to at least partially reflow, thereby fusing or otherwise bonding the longitudinal edges 61, 63 together. For example, similar to previous embodiments, the assembly may be heated to attach the thin-walled sheet 68 to the inner surface of the slotted tube 62 and within the slot.

Excess material from the longitudinal edges 69a, 69b of the thin-walled sheet 68 may remain exposed outside the (no longer slotted) tube 62. This excess material may be cut or otherwise trimmed along the wall of the tube 62, resulting in the tubular device 66 shown in FIG. 5F.

Figure 5E:
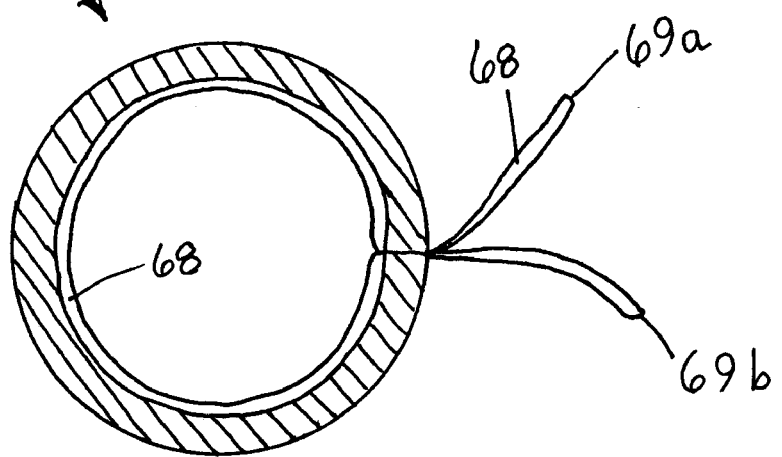
Figure 5F:
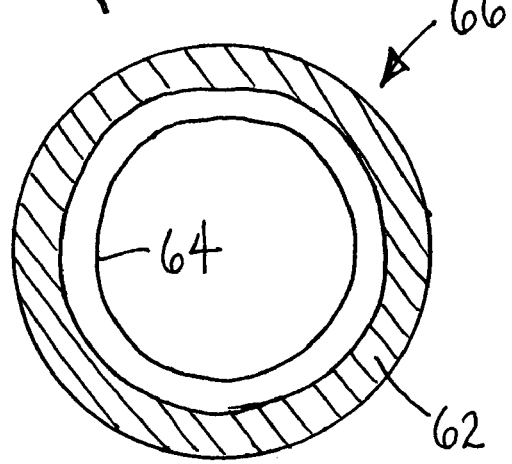

As shown in FIG. 5E, the mandrel 50 is removed from the bonded thin film sheet 68 and slotted tube 62, either before or after trimming the excess longitudinal edges 69a, 69b.

Turning to FIG. 6A-6E, yet another method is shown for making a tubular device, such as apparatus 10 described above. As shown in FIG. 6A, a relatively thick sheet 78 may be provided that includes a first upper surface 74, a second lower surface 75, first and second side edges 77a, 77b, and a thickness 79. The sheet 78 may be formed from one or more layers of material, similar to the tubular structures described elsewhere herein, except provided in a relatively flat configuration (or a concave, convex, or other nonplanar configuration where the first surface 74 is readily accessible, similar to other embodiments herein). In exemplary embodiments the thickness 79 of the sheet 78 may be between about 0.0005-0.2 inch (0.0127-5.08 mm).

Turning to FIG. 6B, the first surface 74 of sheet 78 is coated, e.g., similar to the methods describe elsewhere herein, to provide a substantially uniform thickness coating 88 on the first surface 74. For example, the coating 88 may include a hydrophilic material that provides a desired lubricity to the first surface 74.

As shown is FIGS. 6C and 6D, the coated sheet 78 may be positioned near and rolled around a mandrel 50, which may be similar to other embodiments described herein, with the coated first surface 74 disposed inwardly. As seen in FIG. 6D, after rolling the coated sheet 78, the first side edge 77a may be disposed adjacent the second side edge 77b, thereby providing a tubular structure defining a lumen. The first and second side edges 77a, 77b may then be bonded or otherwise attached to one another, e.g., using heat bonding, lamination, ultrasonic energy, or adhesives, as described elsewhere herein.

As shown in FIG. 6E, once the side edges 77a, 77b are attached to provide a continuous wall tubular device 76, the tubular device 76 may be removed from the mandrel 50, thereby resulting in the tubular device 76 having the lubricious inner surface 74.

Figure 7:
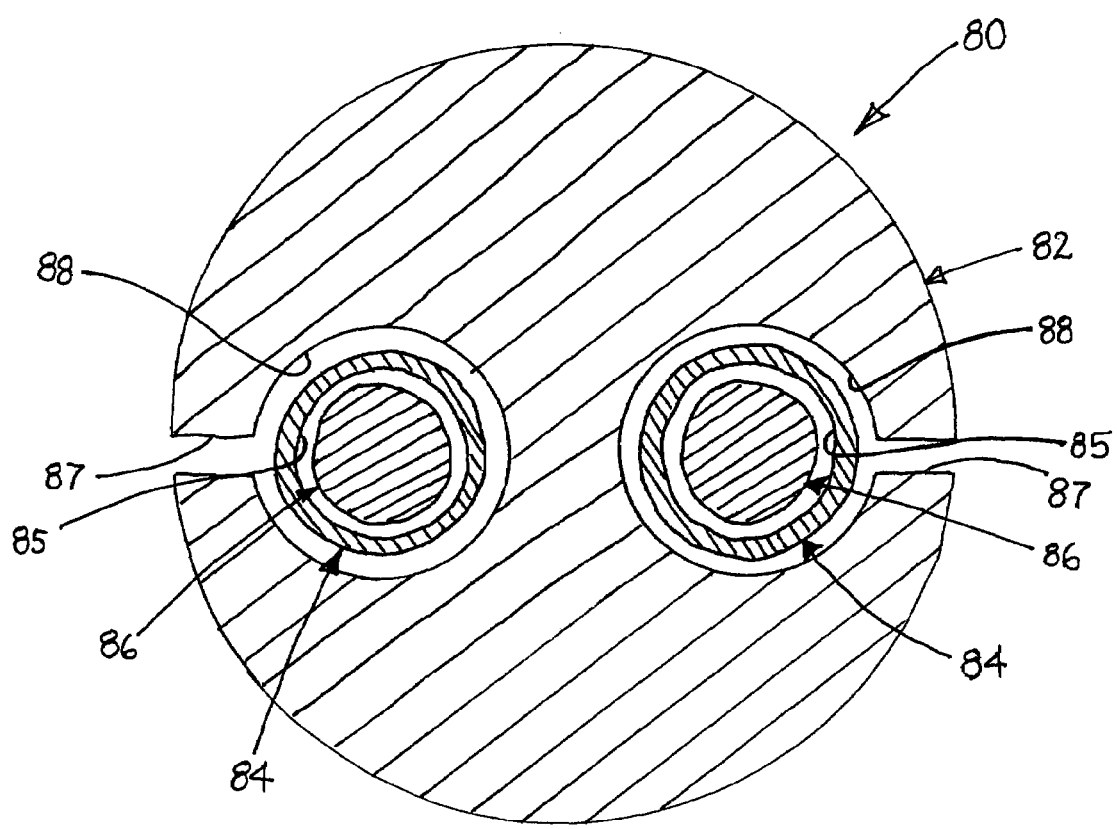
FIG. 7 is a cross-sectional view of a tubular device including a pair of adjacent lumens disposed over a mandrel carrying a coated thin-walled sleeve.

Turning to FIG. 7, another embodiment of a tubular assembly 80 is shown that includes an outer tubular body 82, a pair of thin-walled sleeves 84, and a pair of mandrels 86. Similar to the previous embodiments, the thin-walled sleeves 84 may be formed from flat sheets or tubular sleeves that have a coating on an inner surface 85 thereof. For example, the coating may be applied before the sheet is rolled and formed into the sleeves 84 or while the sleeves 84 are in a tubular form (e.g., by coating an outer surface and inverting the sleeves 84). The sleeves 84 may be positioned around respective mandrels 86, which may also be similar to previous embodiments.

As shown, the outer tubular body 82 includes a pair of lumens 88 extending longitudinally through the tubular body 82. The tubular body 82 may be an extrusion or other single or multiple layer tubular structure, similar to other embodiments described herein. For example, the tubular body 82 may be formed as a continuous walled tube, which may be slit along its length to provide slots 87 communicating with respective lumens 88.

The tubular body 82 may be positioned around the mandrels 86 and thin-walled sleeves 84, similar to the previous embodiments. For example, each slot 87 may be opened sufficiently to insert a mandrel 86 carrying a thin-walled sleeve 84 through the slot 87 into the lumen 88. Alternatively, the mandrels 86 may be inserted longitudinally into the respective lumens 88 with the thin-walled sleeves 84 thereon. In this alternative, it may be possible to eliminate the slots 87.

The tubular body 82 may be attached to the thin-walled sleeves 84, e.g., by heating as described above, thereby reflowing the material of the tubular body 82 to close the slots 87 and provide a continuous wall structure. The mandrels 86 may then be removed, thereby providing a tubular device having lumens 88 having coated inner surfaces. Thus, it will be appreciated that tubular devices may be created that include multiple lumens, each of which may include a desired coating along its inner surface.

Figure 8:
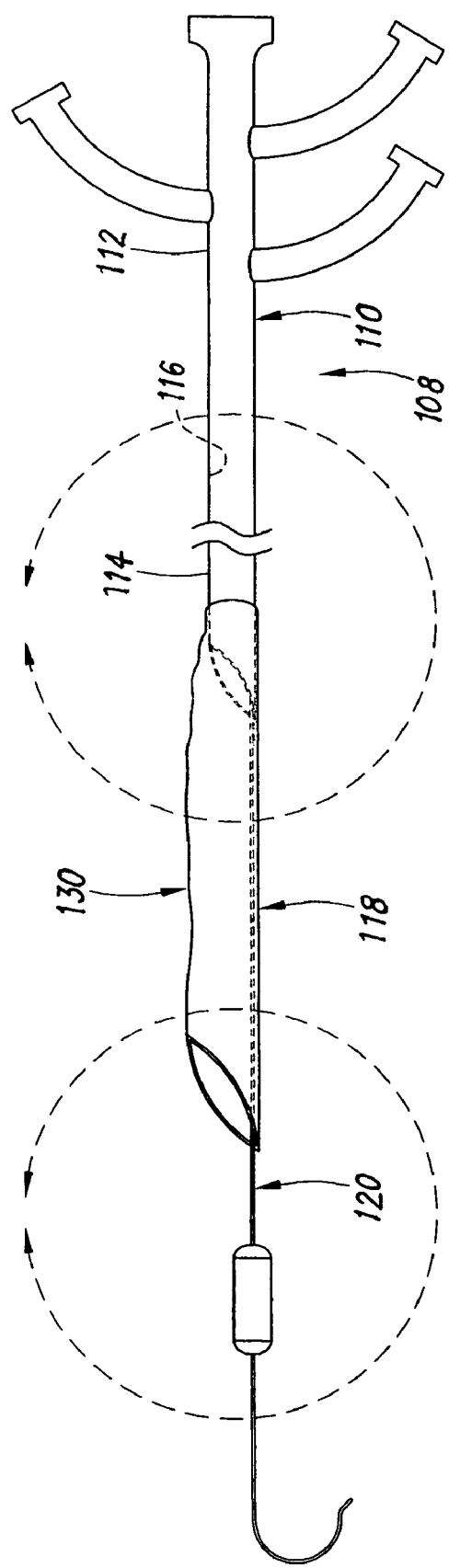
FIG. 8 is a perspective view of an exemplary embodiment of a sheath apparatus, including a tubular proximal portion and an expandable distal portion. The tubular portion includes a lumen with a coated inner surface.

Turning to FIG. 8, an exemplary embodiment of a sheath apparatus 108 is shown that includes a tubular proximal portion 110 and an expandable distal portion 118. The proximal portion 110 may include at least one lumen 116 including a coated liner (not shown), such as any of the embodiments described herein.

Generally, the proximal portion 110 is an elongate tubular member, e.g., a catheter, sheath, and the like, including a proximal end 112, a distal end 114 sized for insertion into a body lumen, and a lumen 116 extending between the proximal and distal ends 112, 114. Optionally, the tubular proximal portion 110 may include one or more additional lumens (not shown), e.g., for receiving a guide wire, inflation media, and/or for perfusion. Such additional lumens may be disposed concentrically around one another or in a side-by-side arrangement.

With continued reference to FIG. 8, the expandable distal portion 118 may include an elongate stiffening member 120 providing a "backbone" for the distal portion 118 and an expandable sheath 130. Additional information on materials and methods for making the apparatus 108 are disclosed in co-pending application Ser. No. 10/423,321, filed Apr. 24, 2003, Ser. No. 10/934,082, filed Sep. 2, 2004, Ser. No. 10/934,305, filed Sep. 2, 2004, and Ser. No. 10/958,034, filed Oct. 4, 2004. The entire disclosures of these applications are expressly incorporated by reference herein.

Figure 9:
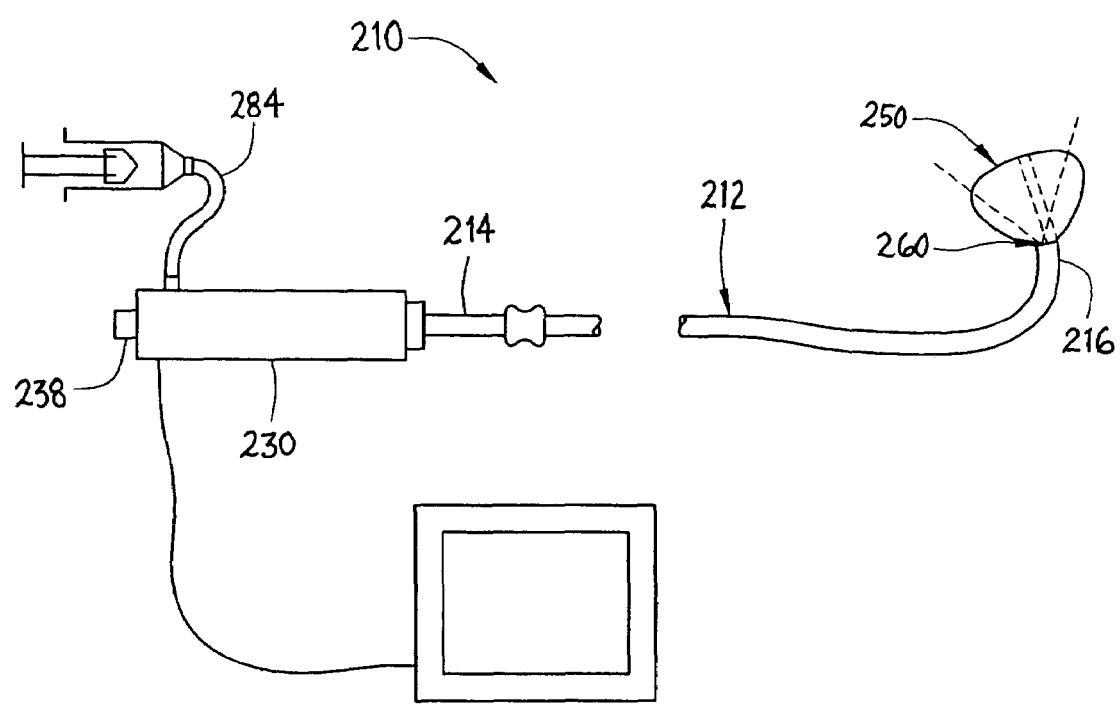
FIG. 9 is a perspective view of an imaging catheter including a lumen, the lumen including a coated inner surface.

Turning to FIG. 9, an exemplary embodiment of an apparatus 210 is shown for imaging a body lumen, e.g., for visualizing, accessing, and/or cannulating a body lumen from a body cavity (not shown). Generally, the apparatus 210 includes a catheter or other elongate member 212, including a handle 230 on a proximal end 214 of the catheter 212, and a balloon or other expandable member 250 on a distal end 216 of the catheter 212. An imaging assembly 260 may be provided on or otherwise carried by the catheter 212 for imaging through the balloon 250, e.g. including one or more illumination fibers and/or imaging optical fibers (not shown) extending through the catheter 212.

The catheter 212 may include one or more lumens (not shown) extending between the proximal and distal ends 214, 216 that may include a coated liner or inner surface, as described elsewhere herein. For example, an accessory lumen may extend from a port 238 in the handle 230 through the balloon 250. The lumen may be coated or otherwise lined to facilitate introducing one or more instruments (not shown) the through the apparatus 210.

Additional information that may relate to the structure and/or methods for making and/or using the apparatus 210 may also be found in co-pending applications Ser. No. 10/447,526, filed May 29, 2003, Ser. No. 11/057,074, filed Feb. 11, 2005, and Ser. No. 11/062,074, filed Feb. 17, 2005. The entire disclosures of these applications are expressly incorporated by reference herein.

Returning to FIGS. 1A and 1B, in another embodiment, a delivery sheath 10 may be provided that includes an inner polyurethane liner 20 having a coating on its inner surface 21. In an exemplary embodiment, the liner 20 may have a thickness between about 0.0001-0.01 inch (0.0127-0.25 mm), or between about 0.0001-0.003 inch. The coating may include any of the embodiments described herein, e.g., a lubricious and/or hydrophilic material applied using any of the methods described herein. For example, the inner liner 20 may be formed from a coated sheet or an inverted tube, as described elsewhere herein.

The sheath 10 may include an outer layer 22 that includes a stainless steel braid (not shown) surrounding the inner liner 20 and a layer of PEBAX or urethane surrounding the braid. In an exemplary embodiment, the layer of PEBAX or urethane may have a thickness between about 0.004-0.02 inch (0.1-0.5 mm). The sheath 10 may define a lumen 16 having a diameter between about one and five millimeters (1-5 mm), depending upon the particular application for the sheath 10.

With continued reference to FIGS. 1A and 1B, in another embodiment, the device 10 may be a core for passage of a guidewire (not shown). In such an embodiment, the inner liner 20 may include a layer of polyurethane having a thickness between about 0.0001-0.0015 inch (0.0025-0.038 mm) thickness. An inner surface 21 of the liner 20 may be coated as described elsewhere herein, e.g., with a lubricious and/or hydrophilic materials. The outer layer 22 may include a tubular body formed from nylon, PEBAX, or urethane having a thickness between about 0.0005-0.006 inch (0.0127-0.076 mm). The resulting device 10 may include a lumen 16 having a diameter between about 0.016-0.045 inch (0.40-1.15 mm).

The device 10 may be provided within a catheter, guidewire, or other tubular device (not shown), which may be constructed in any known manner. The device 10 may be bonded or otherwise attached within a lumen of the tubular device, similar to the methods described above, to provide a lubricious or otherwise coated inner lumen 16.

Figure 10A:
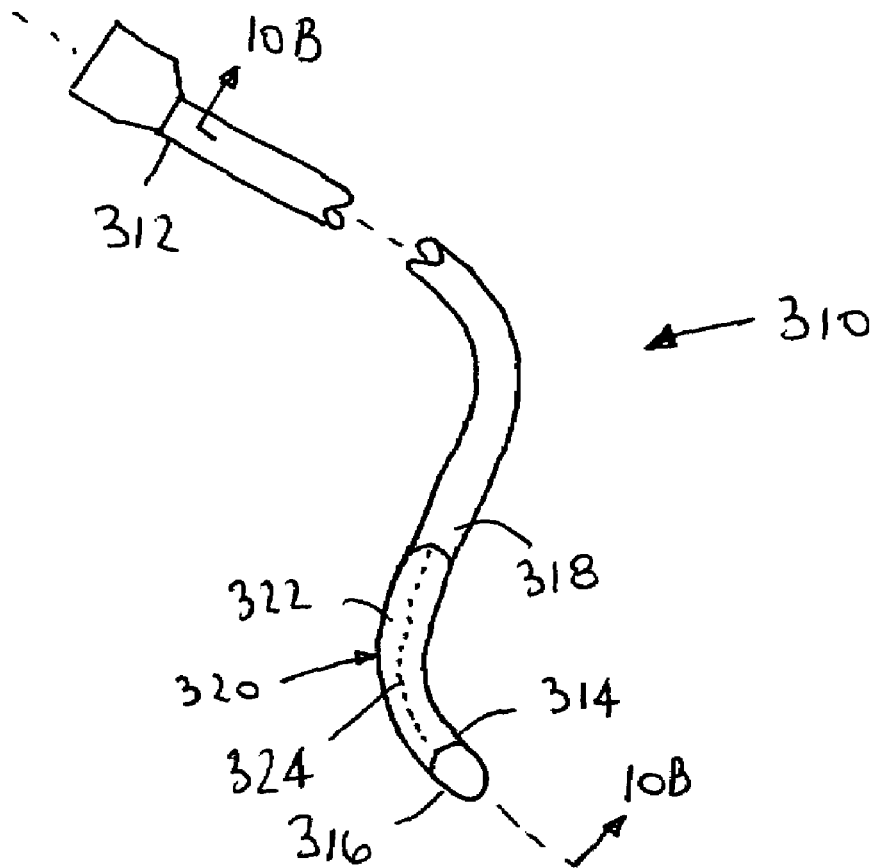
FIG. 10A is a perspective view of an elongate lead including an outer lubricious coating on a portion thereof.
Figure 10B:
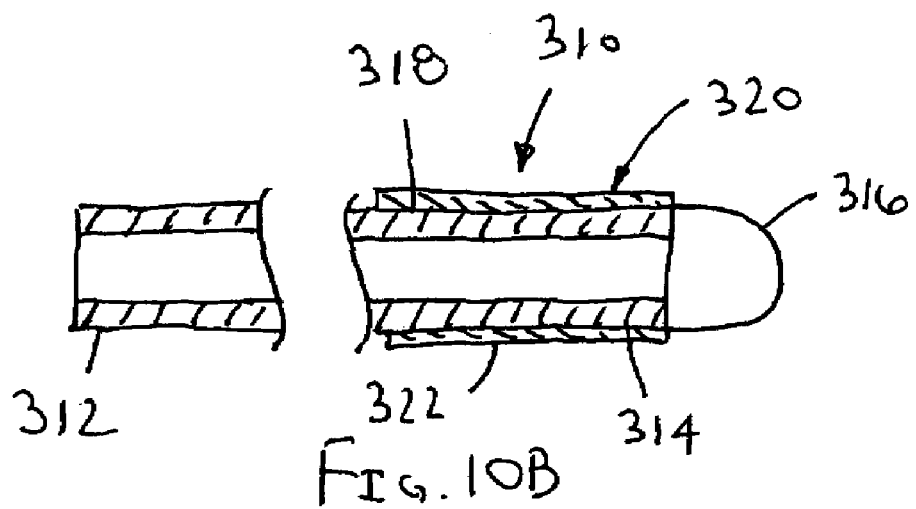
FIG. 10B is a cross-sectional view of the lead of FIG. 10A taken along line 10B-10B.

Turning to FIGS. 10A and 10B, in yet another embodiment, an elongate lead 310 is shown that includes a proximal end 312, a distal end 314 sized and/or shaped for introduction into a patient's vasculature, and one or more electrodes 316 (one shown) on the distal end 314. The lead 310 is formed from a lead body, which may be formed, for example, from silicone, polyurethane, or other materials defining an outer surface 318. The lead body may have a uniform construction along its length or may vary, similar to other embodiments described herein. The lead 310 may include other components, e.g., one or more wires or other conductors (not shown) extending between the electrode(s) and the proximal end 312, one or more mechanical and/or electrical connectors (also not shown) on the proximal end 312, and the like.

The lead 310 includes an outer cover 320 surrounding at least a portion of the outer surface 318. The cover 320 may include a layer of polyurethane, e.g., having a thickness between about 0.00025-0.003 inch (0.0127-0.076 mm). The cover 320 includes a coating on its outer surface 322, which may be any of the coatings described herein, e.g., including a lubricious and/or hydrophilic material.

As best seen in FIG. 10A, the cover 320 extends along the distal end 314 of the lead 310, e.g., immediately adjacent the electrode 316. Alternatively, the cover 320 may extend over the electrode 316 (not shown). In addition or alternatively, the cover 320 may extend proximally from the distal end 314 towards the proximal end 312 (also not shown). In other alternatives, a plurality of covers (not shown) may be provided spaced apart from one another along the length of the lead 310. The covers may include similar or different coatings from one another, depending upon the properties desired for different portions of the lead 310.

As shown in FIG. 10A, the cover 320 may include a weakened seam 324 extending along a length of the cover 320. The seam 324 may be a thin-walled region, a perforated seam, and the like. Optionally, a plurality of weakened seams (not shown) may be provided. The seam 324 may facilitate removal of the cover 320, if desired. In addition, a thread, tab, or other element (not shown) may extend from the cover 320, e.g., to the proximal end 312 of the lead 310. Such an element may be grasped or otherwise manipulated to remove the cover 320, e.g., pulled to cause the seam 324 to tear and peel the cover 320 from around the lead 310.

The cover 320 may be made similar to the liners described above, e.g., as a sheet or tube (but without being inverted). The cover 320 may be simply slid over the lead 310, heat shrunk around the lead 310, or bonded onto the outer surface 318 (depending upon whether the cover 320 is removable).

During use, the lead 310 may be introduced using conventional methods. The cover 320 may facilitate advancing the distal end 314 through tortuous anatomy, e.g., if the cover 320 includes a lubricious coating. Once the lead 310 is positioned at a desired location, the cover 320 may be removed from over the distal end 314. For example, as described above, a tab (not shown) adjacent the proximal end 312 and coupled to the cover 320 may be pulled to tear or otherwise remove the cover 320. Removing the cover 320 may facilitate maintaining the distal end 314 at the desired location, i.e., minimizing migration that may occur of the cover remains over the distal end 314. Optionally, the underlying outer surface 318 of the lead 310 may include materials, features, coatings, and the like that enhance securing the distal end 314 once the cover 320 is removed.

Turning to FIGS. 11A-11G, another method is shown for making a tubular device, such as apparatus 10 described above. Initially, as shown in FIG. 11A, a thin film sheet 310 may be provided including a first upper surface 312 and a second lower surface 314 (not shown in FIG. 11A, see, e.g., FIG. 11C). The sheet 310 may be formed from a single layer or multiple layers of material, similar to the other embodiments described elsewhere herein. In an exemplary embodiment, the sheet 310 may be formed from a sheet of polyurethane, e.g., having a thickness between about 0.0001-0.003 inch (0.0025-0.076 mm). However, other suitable polymers may also be used.

Turning to FIG. 11B, with the sheet 310 substantially flat (or otherwise providing ready access to first surface 312, as described elsewhere herein), a coating 316 is applied to the first surface 312. Alternatively, a pre-formed thin membrane sleeve may be coated on its outer surface and subsequently inverted, as described elsewhere herein. In an exemplary embodiment, the coating may include a hydrophilic material, such as Polyvinylpyrrolidone, sprayed onto the first surface 312. Alternatively, the coating may be applied using other procedures, such as rolling, brushing, spreading by maer rods, or dipping, e.g. on the first surface 312.

The hydrophilic material may provide a predetermined lubricity on the first surface 312. Alternatively or in addition, other materials may be applied to provide one or more desired properties on the first surface 312, e.g. anti-thrombotic or anti-hemolytic materials, drug-eluting coatings, and the like. Alternatively, these materials may also be applied to the second surface (not shown). As a further alternative, other materials, for example, adhesives, primers, reinforcing elements, backing material, and the like, may be applied to the second surface 314, e.g., to facilitate construction or processing of a thin-walled sleeve or a subsequent apparatus, as described elsewhere herein.

Turning to FIG. 11C, the sheet 310 may be folded over such that the first surface 312 is disposed outwardly and the second surface 314 is disposed inwardly. A longitudinal seam 318 may then be created to create a relatively thin-walled sleeve 320. For example, the longitudinal seam may be created by heat bonding, using ultrasonic energy, using one or more adhesives, and/or as otherwise described elsewhere herein. As shown in FIGS. 11C and 11D, excess material 322 may be trimmed from the thin-walled sleeve 320. Turning to FIG. 11E, the thin-walled sleeve 320 may then be inverted, as described elsewhere herein, such that the first surface 312 is now disposed inwardly.

Turning to FIG. 11F, in an alternative embodiment, a thin-walled sleeve may be created by disposing the coated first surface 312' of the thin film sheet 310 inwardly before creating a longitudinal seam (not shown). Using this method, there is no need to invert the thin-walled sleeve 320' in order to dispose the coated first surface 312' inwardly. Optionally, one or more outer layers (not shown) may be bonded or otherwise provided around the thin-walled sleeve 320 or 320,' similar to the other embodiments described elsewhere herein.

Figure 12A:
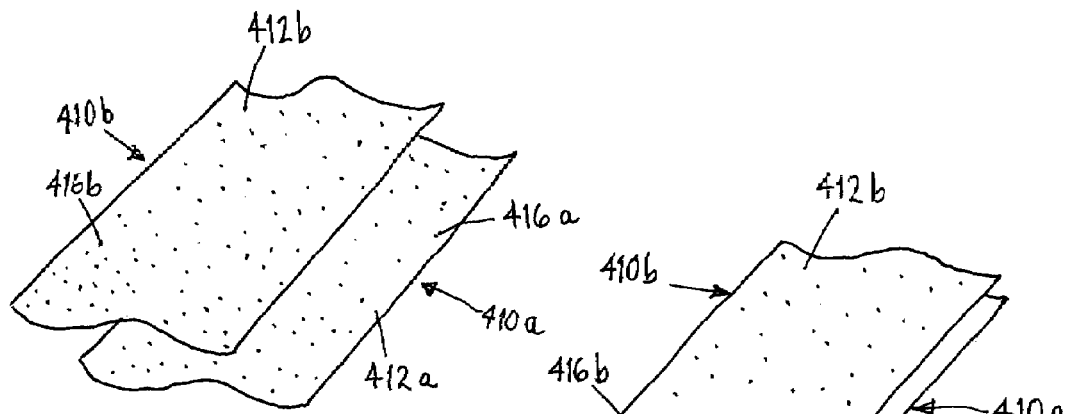
FIGS. 12A-E are perspective views and FIG. 12F is a cross-sectional view, showing another method for making a tubular device including a coated inner surface.

Turning to FIGS. 12A-12F, another method is shown for making a coated thin-walled sleeve. Initially, as shown in FIG. 12A, two thin film sheets 410a, 410b may be provided, similar to the other embodiments described herein. Each sheet 410a, 41b includes a first upper surface 412a, 412b and a second lower surface 414a, 414b (not shown in FIG. 12A). With each sheet 410 substantially flat, a coating 416 may be applied, as described elsewhere herein, to each first surface 412. Optionally, each second surface 414 may also be coated as described elsewhere herein.

Figure 12B:
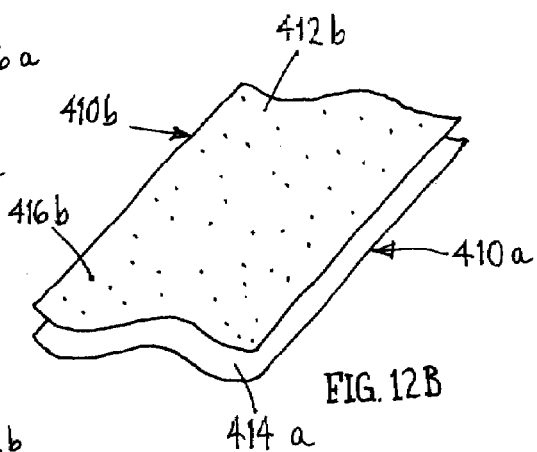
Figure 12C:
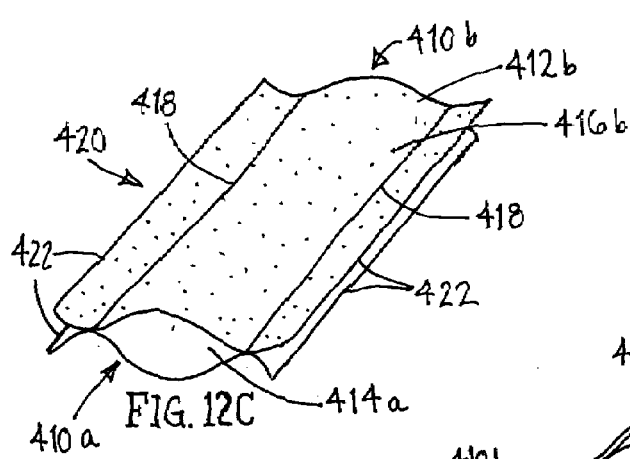
Figure 12D:
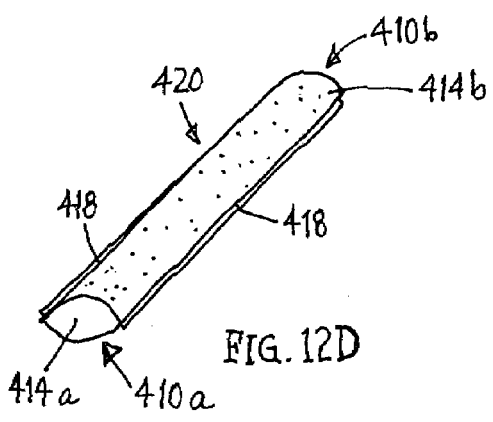
Figure 12E:
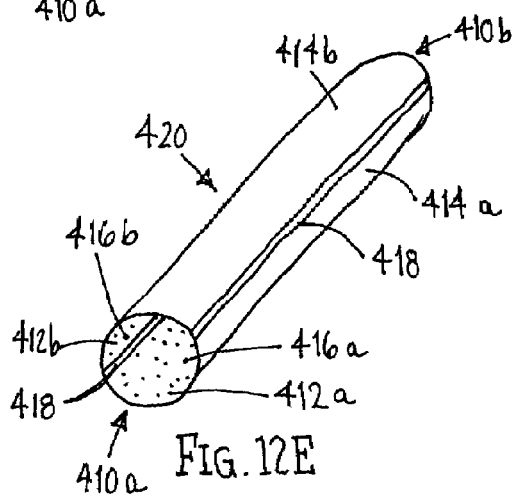

Turning to FIGS. 12B and 12C, the second surfaces 414 of sheets 410 may be placed adjacent to one another and at least two longitudinal seams 418 may then be created to form a relatively thin-walled sleeve 420. Excess material 422 may be trimmed from the thin-walled sleeve 420, as shown in FIG. 12D. Turning to FIG. 12E, the thin-walled sleeve 420 may then be inverted such that the first surfaces 412 are now disposed inwardly.

Figure 12F:
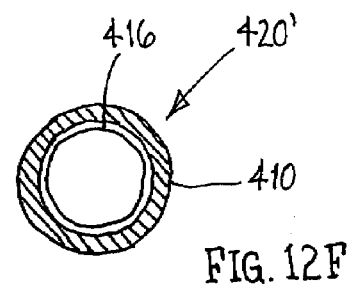

Turning to FIG. 12F, in an alternative embodiment, a thin-walled sleeve 320' may be created by disposing the coated first surfaces 412 of the thin film sheets 410 inwardly before creating the longitudinal seams (not shown). Using this method, there is no need to invert the thin-walled sleeve 420' in order to dispose the coated first surfaces 412 inwardly. In alternative embodiments, other methods may be used, such as those described elsewhere herein, which may include orienting a coated surface such that inversion is not required subsequent to seam creation in order to dispose the coated surface inwardly.

Figure 13A:
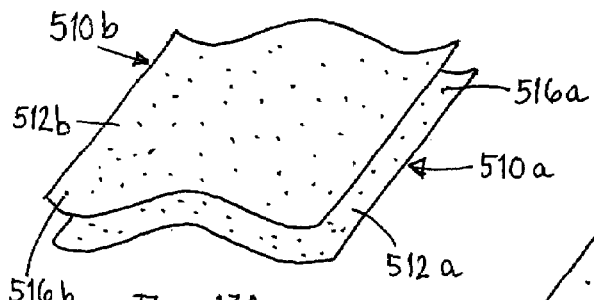
FIGS. 13A-E are perspective views and FIG. 13F is a cross-sectional view, showing another method for making a tubular device including a coated inner surface.

Turning to FIGS. 13A-13F, another method is shown for making coated thin-walled sleeves. Initially, as shown in FIG. 13A, two thin film sheets 510a, 510b may be provided similar to other embodiments wherein, each including a first upper surface 512a, 512b and a second lower surface 514a, 514b (not shown in FIG. 13A). With each sheet 510 substantially flat (or otherwise provided), a coating 516 is applied to each first surface 512, as described elsewhere herein. Optionally, each second surface 514 may also be coated, as described elsewhere herein.

Figure 13B:
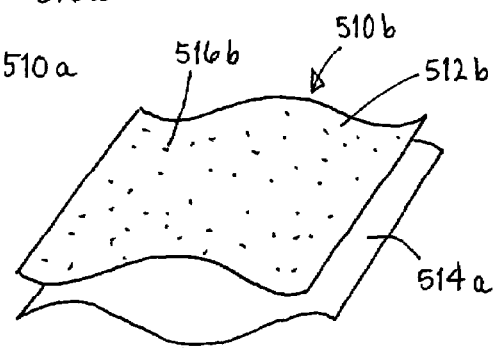
Figure 13C:
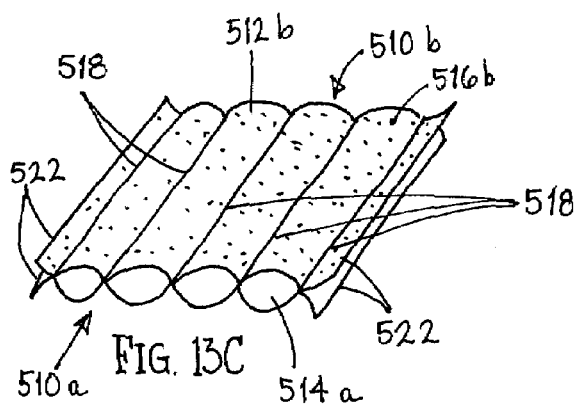
Figure 13D:
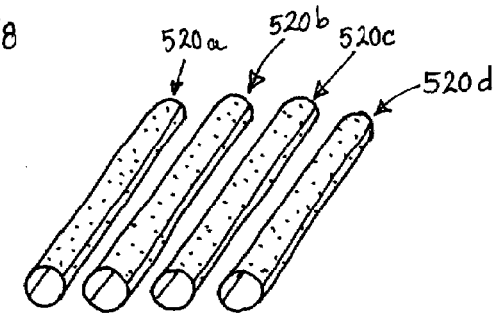

Turning to FIGS. 13B and 13C, the second surfaces 514 of sheets 510 may be placed adjacent to one another and a plurality of (e.g., at least three) longitudinal seams 518 may then be created to form at least two relatively thin-walled sleeves 520. The sleeves 520 may be separated and excess material 522 may be trimmed from the thin-walled sleeves 520, as shown in FIG. 13D. A longitudinal cut may be created at the same time each longitudinal seem 518 is created or subsequent to creating each longitudinal seam 518, thereby, separating adjacent thin-walled sleeves 520 from one another.

Figure 13E:
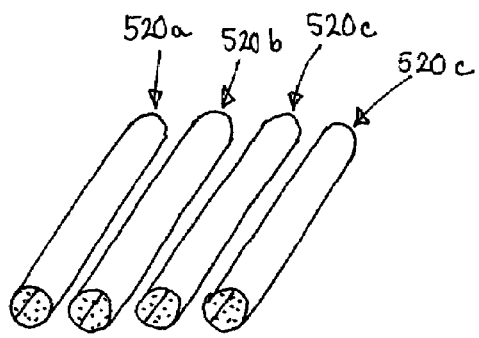

Turning to FIG. 13E, each thin-walled sleeve 520 may be inverted such that the coated first surfaces 512 are now disposed inwardly.

Figure 13F:
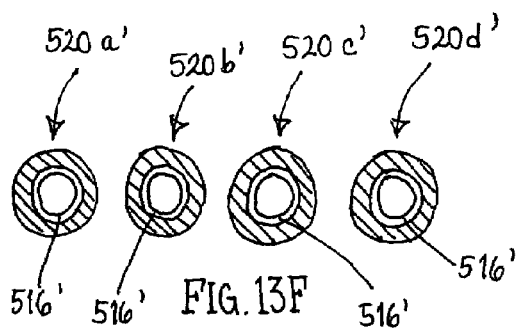

Turning to FIG. 13F, in an alternative embodiment, multiple thin-walled sleeves 520' may be created by disposing the coated first surfaces 516' of the thin film sheets inwardly creating longitudinal searns (not shown). Using this method, there is no need to invert the thin-walled sleeves 520' in order to dispose the coated first surfaces inwardly.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for making a catheter sized for introduction into a body lumen, comprising:
    providing a thin sheet comprising first and second side edges;
    coating a first surface of the thin sheet with a hydrophilic coating;
    thereafter, rolling the thin sheet such that the first and second side edges are disposed adjacent one another and the hydrophilic coating is disposed inwardly;
    creating a longitudinal seam along the first and second side edges of the rolled thin sheet to create a sleeve the sleeve extending substantially the entire length of the tubular structure; and
    attaching a tubular structure around the sleeve.

2. The method of claim 1, wherein providing the thin sheet comprises attaching first and second layers of material together.

3. The method of claim 1, wherein the tubular structure comprises a thickness that is substantially greater than a thickness of the sleeve.

4. The method of claim 1, wherein the tubular structure comprises a reinforcement layer and an outer continuous layer.

5. The method of claim 1, wherein the sleeve and tubular structure are attached together by at least one of laminating, bonding, and heat sealing.

6. The method of claim 1, wherein the thin sheet comprises polyurethane and the tubular structure comprises at least one of polyether block amide and Urethane.

7. The method of claim 6, wherein the sheet comprises Ester-based polyurethane.

8. The method of claim 1, further comprises removing excess material along the longitudinal seam, thereby removing a portion of the first and second side edges.

9. The method of claim 1, wherein the step of attaching the tubular structure around the sleeve comprises:
    positioning the sleeve around a mandrel to create a first assembly; and
    positioning the tubular structure over the first assembly to create a second assembly.

10. The method of claim 9, wherein the step of attaching the tubular structure around the sleeve further comprises:
    positioning heat shrink tubing over the second assembly;
    heating the heat shrink tubing; and
    removing the shrink tubing from around the second assembly.

11. The method of claim 9, further comprising removing the mandrel after attaching the tubular structure to the sleeve.

12. A method for making a tubular device sized for introduction into a body lumen, comprising:
- coating a first surface of a thin sheet with a coating imparting one or more desired properties to the first surface;
- wrapping the thin sheet at least partially around a mandrel with the first surface disposed inwardly;
- positioning a slotted tube around the thin sheet and mandrel;
- attaching the slotted tube to the thin sheet to form a tubular structure; and
- removing the tubular structure from the mandrel,
- wherein the slotted tube comprises longitudinal edges defining a slot, and wherein the slotted tube is positioned around the thin sheet and mandrel by separating the longitudinal edges.

13. The method of claim 12, further comprising trimming excess edges of the thin sheet from the tubular structure.

14. The method of claim 12, wherein the slotted tube is attached to the thin sheet by at least one of lamination, bonding, and heat-sealing.

15. The method of claim 12, wherein the longitudinal edges are bonded together when the slotted tube is attached to the thin sheet.

16. The method of claim 12, wherein the slotted tube comprises a thickness that is substantially greater than a thickness of the thin sheet.

17. The method of claim 12, wherein the slotted tube comprises a reinforcement layer and an outer layer.

18. The method of claim 12, wherein the thin sheet comprises polyurethane and the slotted tube comprises at least one of polyether block amide and Urethane.

19. The method of claim 12, wherein the coating comprises a hydrophilic material.

20. The method of claim 12, wherein the one or more desired properties comprise a predetermined lubricity.

21. The method of claim 12, wherein the slotted tube is attached to the thin sheet by directing the slotted tube, thin sheet, and mandrel through a heated die.

22. The method of claim 12, wherein the tubular structure is formed by a continuous process.

23. A method for making a catheter sized for introduction into a body lumen and having proximal and distal ends, comprising:
- providing a sheet of material comprising a first surface and a second surface;
- coating the first surface of the sheet with a hydrophilic coating to impart the first surface with a predetermined lubricity; and
- thereafter, rolling the sheet until longitudinal edges of the sheet are disposed adjacent one another; and
- attaching the longitudinal edges of the rolled sheet to one another to form a continuous wall defining a lumen the rolled sheet extending between the proximal and distal ends of the catheter.

24. The method of claim 23, wherein the longitudinal edges are attached to one another by using at least one of heat bonding, an adhesive, and lamination.

25. A method for making a catheter sized for introduction into a body lumen, comprising:
- providing a thin sheet comprising a first surface and a second surface;
- coating the first surface with a coating to impart the first surface with one or more desired properties;
- after coating the first surface, rolling the sheet such that the first and second side edges are disposed adjacent one another and extend longitudinally, and the coated first surface is disposed inwardly and the second surface of the sheet is disposed outwardly; and
- after rolling the sheet the sheet extending between the proximal and distal ends of the tubular structure, attaching a tubular structure having proximal and distal ends around the rolled sheet, thereby providing a tubular device comprising an inner surface with the one or more desired properties.

26. A method for making a catheter sized for introduction into a body lumen, comprising:
- providing a sheet of thermoplastic material having first and second surfaces and comprising first and second side edges;
- coating the first surface of the sheet with a hydrophilic coating;
- thereafter rolling the sheet such that the first and second side edges are disposed adjacent one another and the coated first surface is disposed inwardly and the second surface of the sheet is disposed outwardly;
- positioning a tubular structure having proximal and distal ends around the rolled sheet, the tubular structure having a thickness that is substantially greater than a thickness of the rolled sheet extending between the proximal and distal ends of the tubular structure the sheet; and
- heating at least one of the tubular structure and the rolled sheet to bond the second surface of the sheet to the tubular structure.

27. The method of claim 26, wherein the rolled sheet is heated to cause the thermoplastic material of the sheet to reflow and bond to the tubular structure.

28. The method of claim 26, further comprising creating a longitudinal seam along the first and second side edge to create a sleeve before positioning the tubular structure around the rolled sheet.

29. The method of claim 26, wherein positioning the tubular structure around the rolled sheet comprises placing a reinforcement layer against the second surface of the sheet placing a substantially uniform outer layer against the reinforcement layer.

30. The method of claim 26, wherein the sheet comprises at least one of polyurethane and polyether block amide, and the tubular structure comprises at least one of polyether block amide and urethane.

31. The method of claim 26, wherein the sheet is rolled around a mandrel to create a first assembly, and the tubular structure is positioned over the first assembly to create a second assembly.

32. The method of claim 31, wherein heating at least one of the tubular structure and the rolled sheet comprises:
- positioning heat shrink tubing over the second assembly; and
- heating the heat shrink tubing to cause the sheet to reflow and bond to the tubular structure.

33. The method of claim 31, further comprising removing the mandrel and the heat shrink tubing after bonding the sheet to the tubular structure.

34. The method of claim 26, wherein the sheet has a thickness between about 0.0001-0.003 inch (0.0025-0.076 mm).

* * * * *